United States Patent
Reid et al.

(10) Patent No.: US 12,351,867 B2
(45) Date of Patent: *Jul. 8, 2025

(54) ANALYSIS OF A POLYNUCLEOTIDE VIA A NANOPORE SYSTEM

(71) Applicant: Oxford Nanopore Technologies PLC, Oxford (GB)

(72) Inventors: Stuart William Reid, Oxford (GB); Gavin Harper, Sonning (GB)

(73) Assignee: Oxford Nanopore Technologies PLC, Oxford (GB)

( * ) Notice: Subject to any disclaimer, the term of this patent is extended or adjusted under 35 U.S.C. 154(b) by 945 days.

This patent is subject to a terminal disclaimer.

(21) Appl. No.: 17/369,834

(22) Filed: Jul. 7, 2021

(65) Prior Publication Data
US 2022/0064724 A1 Mar. 3, 2022

Related U.S. Application Data

(63) Continuation of application No. 16/162,848, filed on Oct. 17, 2018, now Pat. No. 11,085,077, which is a continuation of application No. 14/653,656, filed as application No. PCT/GB2013/053359 on Dec. 19, 2013, now Pat. No. 10,131,943.

(30) Foreign Application Priority Data

Dec. 19, 2012 (GB) ..................................... 1222928

(51) Int. Cl.
C12Q 1/6869 (2018.01)
C12Q 1/6806 (2018.01)

(52) U.S. Cl.
CPC ......... *C12Q 1/6869* (2013.01); *C12Q 1/6806* (2013.01)

(58) Field of Classification Search
None
See application file for complete search history.

(56) References Cited

U.S. PATENT DOCUMENTS

| | | | |
|---|---|---|---|
| 5,795,782 A | 8/1998 | Church et al. | |
| 6,128,587 A | 10/2000 | Sjolander | |
| 7,625,706 B2 | 12/2009 | Akeson et al. | |
| 7,731,826 B2 | 6/2010 | Hibbs et al. | |
| 8,324,914 B2 | 12/2012 | Chen et al. | |
| 8,452,546 B1 | 5/2013 | Lathrop | |
| 9,057,102 B2 | 6/2015 | Turner et al. | |
| 9,121,064 B2 | 9/2015 | Turner et al. | |
| 9,127,313 B2 | 9/2015 | Brown et al. | |
| 9,546,400 B2 | 1/2017 | Turner et al. | |
| 9,556,480 B2 | 1/2017 | Turner et al. | |
| 9,678,056 B2 | 6/2017 | Turner et al. | |
| 9,738,929 B2 | 8/2017 | Turner et al. | |
| 10,131,943 B2 | 11/2018 | Reid et al. | |
| 10,260,093 B2 * | 4/2019 | Geiser | B82Y 15/00 |
| 10,689,697 B2 | 6/2020 | Reid et al. | |
| 11,085,077 B2 | 8/2021 | Reid et al. | |
| 11,401,549 B2 | 8/2022 | Reid et al. | |
| 2002/0197618 A1 | 12/2002 | Sampson | |
| 2003/0099951 A1 | 5/2003 | Akeson et al. | |
| 2005/0159898 A1 | 7/2005 | Yasuda | |
| 2005/0202444 A1 | 9/2005 | Zhu | |
| 2005/0272923 A1 | 12/2005 | Zhang et al. | |
| 2006/0019259 A1 | 1/2006 | Joyce | |
| 2006/0086626 A1 | 4/2006 | Joyce | |
| 2007/0161028 A1 | 7/2007 | Schwartz et al. | |
| 2009/0035777 A1 * | 2/2009 | Kokoris | C12Q 1/6806 435/6.12 |
| 2010/0331194 A1 | 12/2010 | Turner et al. | |
| 2011/0121840 A1 | 5/2011 | Sanghera et al. | |

(Continued)

FOREIGN PATENT DOCUMENTS

| | | | |
|---|---|---|---|
| EP | 1351183 A2 | 10/2003 | |
| EP | 1544310 A2 | 6/2005 | |

(Continued)

OTHER PUBLICATIONS

International Search Report and Written Opinion for Application No. PCT/GB2013/053359, mailed Mar. 7, 2014.
International Preliminary Report on Patentability for Application No. PCT/GB2015/053083, mailed Jul. 2, 2015.
[No Author Listed], Chapter 2: Polymerizer Module from Polymer. 1997. 14 pages.
Ainsleigh et al., Hidden Gauss-Markov Models for Signal Classification. IEEE Trans Sig Proc. Jun. 2002;50(6):1355-1367.
Alcock et al., Time-series Similarity Queries Employing a Feature-Based Approach. Proceedings of the 7th Hellenic Conference on Informatics (HCI '99); University of Ioannina, Greece, pp. 1-9, Aug. 26-29, 1999.

(Continued)

*Primary Examiner* — Samuel C Woolwine
(74) *Attorney, Agent, or Firm* — Wolf, Greenfield & Sacks, P.C.

(57) ABSTRACT

A target polynucleotide is expanded. In respect of each nucleotide in the target polynucleotide, the target polynucleotide comprises clock nucleotides and at least one signal nucleotide in a predetermined order. The clock nucleotides have a predetermined sequence common to each nucleotide in the target polynucleotide. The at least one signal nucleotide is characteristic of the identity of the respective nucleotide in the target polynucleotide. During translocation of the expanded polynucleotide through a nanopore, electrical measurements dependent on the polynucleotide within the pore are made, to derive an analysis signal. Clock signals derived from the clock nucleotides are identified. Relative to the positions of the identified clock signals, nucleotide signals derived from the least one signal nucleotide are derived to analyse the target polynucleotide. The predetermined sequence of the clock nucleotides comprises a restriction site for a restriction enzyme and at least one further nucleotide that extends the predetermined sequence.

24 Claims, 8 Drawing Sheets

Specification includes a Sequence Listing.

(56) References Cited

U.S. PATENT DOCUMENTS

| | | | |
|---|---|---|---|
| 2011/0124518 A1* | 5/2011 | Cantor | C12Q 1/6818 977/832 |
| 2011/0226623 A1 | 9/2011 | Timp et al. | |
| 2012/0071330 A1* | 3/2012 | Kokoris | C12Q 1/6825 506/4 |
| 2012/0088235 A1* | 4/2012 | Kokoris | C12P 19/34 204/451 |
| 2012/0316075 A1* | 12/2012 | Buzby | C12Q 1/6869 977/902 |
| 2013/0023423 A1 | 1/2013 | Kavanagh et al. | |
| 2013/0071837 A1 | 3/2013 | Winters-Hilt et al. | |
| 2013/0146456 A1 | 6/2013 | Gundlach et al. | |
| 2013/0203610 A1* | 8/2013 | Meller | C12Q 1/682 506/6 |
| 2014/0255918 A1 | 9/2014 | Olasagasti et al. | |
| 2015/0057948 A1 | 2/2015 | Reid et al. | |
| 2015/0152492 A1 | 6/2015 | Brown et al. | |
| 2015/0152495 A1 | 6/2015 | Stava et al. | |
| 2015/0344944 A1 | 12/2015 | Reid et al. | |
| 2016/0162634 A1 | 6/2016 | Reid et al. | |
| 2017/0091427 A1 | 3/2017 | Massingham | |
| 2017/0096703 A1 | 4/2017 | Dolan et al. | |
| 2017/0219557 A1 | 8/2017 | Reid et al. | |
| 2017/0233804 A1 | 8/2017 | Reid et al. | |
| 2019/0154655 A1 | 5/2019 | Reid et al. | |
| 2019/0203286 A1 | 7/2019 | Reid et al. | |
| 2019/0310242 A1 | 10/2019 | Reid et al. | |
| 2021/0079460 A1 | 3/2021 | Reid et al. | |
| 2023/0167494 A1 | 6/2023 | Reid et al. | |

FOREIGN PATENT DOCUMENTS

| | | |
|---|---|---|
| JP | H11-178575 A | 7/1999 |
| JP | 2002-325581 A | 11/2002 |
| JP | 2005-257687 A | 9/2005 |
| JP | 2006-119140 A | 5/2006 |
| JP | 2010-524436 A | 7/2010 |
| JP | 2010-539966 A | 12/2010 |
| JP | 2014-531901 A | 12/2014 |
| WO | WO 2000/028312 A1 | 5/2000 |
| WO | WO 2000/039333 A1 | 7/2000 |
| WO | WO 2000/079257 A1 | 12/2000 |
| WO | WO 2002/042496 A2 | 5/2002 |
| WO | WO 2005/124888 A1 | 12/2005 |
| WO | WO 2006/028508 A2 | 3/2006 |
| WO | WO 2006/100484 A2 | 9/2006 |
| WO | WO 2007/117832 A2 | 10/2007 |
| WO | WO 2007/137225 A2 | 11/2007 |
| WO | WO 2008/092760 A1 | 8/2008 |
| WO | WO 2008/102120 A1 | 8/2008 |
| WO | WO 2008/102121 A1 | 8/2008 |
| WO | WO 2008/124107 A1 | 10/2008 |
| WO | WO 2009/035647 A1 | 3/2009 |
| WO | WO 2009/077734 A2 | 6/2009 |
| WO | WO 2010/004265 A1 | 1/2010 |
| WO | WO 2010/004273 A1 | 1/2010 |
| WO | WO 2010/034018 A2 | 3/2010 |
| WO | WO 2010/053820 A1 | 5/2010 |
| WO | WO 2010/055307 A1 | 5/2010 |
| WO | WO 2010/086603 A1 | 8/2010 |
| WO | WO 2010/086622 A1 | 8/2010 |
| WO | WO 2010/109107 A1 | 9/2010 |
| WO | WO 2010/109197 A2 | 9/2010 |
| WO | WO 2010/117470 A2 | 10/2010 |
| WO | WO 2010/122293 A1 | 10/2010 |
| WO | WO 2011/046706 A1 | 4/2011 |
| WO | WO 2011/067559 A1 | 6/2011 |
| WO | WO 2012/005857 A1 | 1/2012 |
| WO | WO 2012/021149 A1 | 2/2012 |
| WO | WO 2012/033524 A2 | 3/2012 |
| WO | WO 2012/107778 A2 | 8/2012 |
| WO | WO 2012/109483 A2 | 8/2012 |
| WO | WO 2012/135658 A2 | 10/2012 |
| WO | WO 2012/138357 A1 | 10/2012 |
| WO | WO 2012/164270 A1 | 12/2012 |
| WO | WO 2013/014451 A1 | 1/2013 |
| WO | WO 2013/041878 A1 | 3/2013 |
| WO | WO 2013/057495 A2 | 4/2013 |
| WO | WO 2013/098561 A1 | 7/2013 |
| WO | WO 2013/098562 A2 | 7/2013 |
| WO | WO 2013/109970 A1 | 7/2013 |
| WO | WO 2013/121224 A1 | 8/2013 |
| WO | WO 2013/123379 A2 | 8/2013 |
| WO | WO 2013/153359 A1 | 10/2013 |
| WO | WO 2013/159042 A1 | 10/2013 |
| WO | WO 2013/185137 A1 | 12/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/064443 A1 | 5/2014 |
| WO | WO 2014/064444 A1 | 5/2014 |
| WO | WO 2014/096830 A1 | 6/2014 |

OTHER PUBLICATIONS

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Ashkenasy et al., Recognizing a single base in an individual DNA strand: a step toward DNA sequencing in nanopores. Angew Chem Int Ed Engl. Feb. 18, 2005;44(9):1401-4.

Bates et al., Dynamics of DNA molecules in a membrane channel probed by active control techniques. Biophys J. 2003;84(4):2366-2372. doi:10.1016/S0006-3495(03)75042-5.

Batzoglou, Algorithmic challenges in mammalian whole-genome sequence assembly. In: Encyclopedia of genomics, proteomics and bioinformatics. John Wiley and Sons, New York. 2005.

Bell et al., DNA origami nanopores. Nano Lett. Jan. 11, 2012;12(1):512-7. doi: 10.1021/nl204098n. Epub Dec. 29, 2011.

Bokhari et al., A parallel graph decomposition algorithm for DNA sequencing with nanopores. Bioinformatics. Apr. 1, 2005;21(7):889-96. Epub Nov. 11, 2004.

Boufounos et al., Basecalling using hidden Markov models. Journal of the Franklin Institute, vol. 341:23-36 (2004).

Braha et al., Designed protein pores as components for biosensors. Chem Biol. Jul. 1997;4(7):497-505.

Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.

Case 1:17-cv-00275-LPS Document 18. Notice of subsequent events relating to Oxford's motion to dismiss (D.I. 9). Oct. 18, 2017.

Case 1:17-cv-00275-LPS Document 19. Oxford Nanopore Technologies, Inc.'s response to Pacific Biosciences of California, Inc.'s notice of subsequent events. Oct. 24, 2017.

Case 1:17-cv-00275-RGA Document 10. Oxford's opening brief in support of its motion to dismiss PacBio's complaint for patent infringement. May 8, 2017.

Case 1:17-cv-00275-RGA Document 14. PacBio's response to Oxford's motion to dismiss. Jun. 5, 2017.

Case 1:17-cv-00275-RGA Document 16. Oxford's reply brief in support of its motion to dismiss PacBio's complaint for patent infringement. Jun. 26, 2017.

Case 1:17-cv-01353-LPS Document 13. First Amended Complaint for Patent Infringement. Nov. 30, 2017.

Case 1:17-cv-01353-LPS Document 15. Plaintiff's response to Oxford Nanopore Techologies, Inc.'s Motion to Dismiss and Request for Scheduling Conference. Nov. 30, 2017.

Case 1:17-cv-01353-RGA Document 10. Oxford's opening brief in support of its motion to partially dismiss Pacbio's complaint for patent infringement. Nov. 16, 2017.

Chao et al., Constrained sequence alignment. Bull Math Biol. May 1993;55(3):503-24.

Churbanov et al., Duration learning for analysis of nanopore ionic current blockades. BMC Bioinformatics. Nov. 1, 2007;8 Suppl 7(Suppl 7):S14. doi: 10.1186/1471-2105-8-S7-S14.

(56) References Cited

OTHER PUBLICATIONS

Clarke et al., Continuous base identification for single-molecule nanopore DNA sequencing. Nat Nanotechnol. Apr. 2009;4(4):265-70. doi: 10.1038/nnano.2009.12. Epub Feb. 22, 2009.
Dahl et al., Direct observation of translocation in individual DNA polymerase complexes. J Biol Chem. Apr. 13, 2012;287(16):13407-21. doi:10.1074/jbc.M111.338418. Epub Feb. 29, 2012.
Derrington et al., Nanopore DNA sequencing with MspA. Proc Natl Acad Sci U S A. Sep. 14, 2010;107(37):16060-5. doi: 10.1073/pnas.1001831107.
Devereux et al., A comprehensive set of sequence analysis programs for the VAX. Nucleic Acids Res. Jan. 11, 1984;12(1 Pt 1):387-95.
Edgar, Muscle: multiple sequence alignment with high accuracy and high throughput. Nucleic Acids Res. Mar. 19, 2004;32(5):1792-7. Print 2004.
EP Communication pursuant to Rule 114(2) EPC for Application No. 13706058.8 dated Oct. 19, 2017.
Ervin et al., Simultaneous alternating and direct current readout of protein ion channel blocking events using glass nanopore membranes. Anal Chem. Mar. 15, 2008;80(6):2069-76. doi: 10.1021/ac7021103. Epub Feb. 23, 2008.
Fariselli et al., A new decoding algorithm for hidden Markov models improves the prediction of the topology of all-beta membrane proteins. BMC Bioinformatics. Dec. 1, 2005;6 Suppl 4:S12.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Gordon, Classification. 2nd edition. Chapman and Hall/CRC. 69-109. 1999.
Hall et al., Hybrid pore formation by directed insertion of ?-haemolysin into solid-state nanopores. Nat Nanotechnol. Dec. 2010;5(12):874-7. doi: 10.1038/nnano.2010.237. Epub Nov. 28, 2010.
He et al., Controlling DNA translocation through gate modulation of nanopore wall surface charges. ACS Nano. Jul. 26, 2011;5(7):5509-18. doi: 10.1021/nn201883b. Epub Jun. 17, 2011.
Healy, Nanopore-based single-molecule DNA analysis. Nanomedicine (Lond). Aug. 2007;2(4):459-81.
Hein et al., Statistical alignment:computational properties, homology testing and goodness-of-fit. J Mol Biol. Sep. 8, 2000;302(1):265-79.
Heron et al., Simultaneous measurement of ionic current and fluorescence from single protein pores. J Am Chem Soc. Feb. 11, 2009;131(5):1652-3. doi: 10.1021/ja808128s.
Higgins et al., CLUSTAL: a package for performing multiple sequence alignment on a microcomputer. Gene. Dec. 15, 1988;73(1):237-44.
Ivanov et al., DNA tunneling detector embedded in a nanopore. Nano Lett. Jan. 12, 2011;11(1):279-85. doi: 10.1021/nl103873a. Epub Dec. 6, 2010.
Jain et al., Improved data analysis for the MinION nanopore sequencer. Nat Methods. Apr. 2015; 12(4): 351-356. EPub Feb. 16, 2015. doi: 10.1038/nmeth.3290. Author Manuscript.
Karp et al., Efficient randomized pattern-matching algorithms. IBM J. Res. Development. 1987;31(2):249-260.
Kasianowicz et al., Nanoscopic porous sensors. Annu Rev Anal Chem (Palo Alto Calif). 2008;1:737-66. doi:10.1146/annurev.anchem. 1.031207.112818.
Kaxiras et al. Multiscale simulations of complex systems: computation meets reality. Sci Model Simul. 2008; 15:59-65.
Kent, Blat—the BLAST-like alignment tool. Genome Res. Apr. 2002;12(4):656-64.
Khreich et al., A survey of techniques for incremental learning of HMM parameters. J Info Sciences. Aug. 2012;197:105-130.
Kowalczyk et al., Slowing down DNA translocation through a nanopore in lithium chloride. Nano Lett. Feb. 8, 2012;12(2):1038-44. doi: 10.1021/nl204273h. Epub Jan. 27, 2012.
Lam et al., HMMCONVERTER 1.0: a toolbox for hidden Markov models. Nucleic Acids Res. Nov. 2009;37(21):e139. doi: 10.1093/nar/gkp662.

Lathrop et al., Monitoring the escape of DNA from a nanopore using an alternating current signal. J Am Chem Soc. Feb. 17, 2010;132(6):1878-85. doi:10.1021/ja906951g.
Liang et al., Bayesian Basecalling for DNA Sequence Analysis using Hidden Markov Models. Proceedings of 2006 IEEE Conference on Information Sciences and Systems, CISS, pp. 1599-1604 (2006).
Lieberman et al., Processive replication of single DNA molecules in a nanopore catalyzed by phi29 DNA polymerase. J Am Chem Soc. Dec. 22, 2010;132(50):17961-72. doi: 10.1021/ja1087612. Epub Dec. 1, 2010.
Loose et al., Real-time selective sequencing using nanopore technology. Nat Methods. Sep. 2016; 13(9): 751-754. EPub Jul. 25, 2016. doi: 10.1038/nmeth.3930.
Luan et al., Base-by-base ratcheting of single stranded DNA through a solid-state nanopore. Phys Rev Lett. Jun. 11, 2010;104(23):238103. Epub Jun. 10, 2010.
Luan et al., Control and reversal of the electrophoretic force on DNA in a charged nanopore. J Phys Condens Matter. Nov. 17, 2010;22(45):454123. doi:10.1088/0953-8984/22/45/454123. Epub Oct. 29, 2010.
Manrao et al., Reading DNA at single-nucleotide resolution with a mutant MspA nanopore and phi29 DNA polymerase. Nat Biotechnol. Mar. 25, 2012;30(4):349-53. doi: 10.1038/nbt.2171.
Mikheyev et al., A first look at the Oxford Nanopore MinION sequencer. Mol Ecol Resour. Nov. 2014;14(6):1097-102. doi: 10.1111/1755-0998.12324. Epub Sep. 24, 2014.
Montal et al., Formation of bimolecular membranes from lipid monolayers and a study of their electrical properties. Proc Natl Acad Sci U S A. Dec. 1972;69(12):3561-6.
Nakane et al. Nanopore sensors for nucleic acid analysis. J. Phys.: Condens. Matter 15 (2003) R1365-R1393.
Olasagasti et al., Replication of individual DNA molecules under electronic control using a protein nanopore. Nat Nanotechnol. Nov. 2010;5(11):798-806. doi: 10.1038/nnano.2010.177. Epub Sep. 26, 2010.
Pylkkönen et al., Duration Modeling Techniques for Continuous Speech Recognition. Eighth International Conference on Spoken Language Processing. 2004. 4 pages.
Quinlan et al., C.45: Programs for Machine Learning. Morgan Kaufmann Publishers, ISBN 1-55860-238-0. Ed.: Langley. 1-114. 1993.
Schneider et al., DNA sequencing with nanopores. Nat Biotechnol. Apr. 10, 2012;30(4):326-8. doi: 10.1038/nbt.2181.
Soni et al., Synchronous optical and electrical detection of biomolecules traversing through solid-state nanopores. Rev Sci Instrum. Jan. 2010;81(1):014301. doi: 10.1063/1.3277116.
Stoddart et al., Multiple base-recognition sites in a biological nanopore: two heads are better than one. Angew Chem Int Ed Engl. 2010;49(3):556-9. doi: 10.1002/anie.200905483.
Stoddart et al., Nucleobase recognition in ssDNA at the central constriction of the alpha-hemolysin pore. Nano Lett. Sep. 8, 2010;10(9):3633-7. doi: 10.1021/nl101955a.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas. 0901054106. Epub Apr. 20, 2009.
Suzuki et al., A New Hmnet Construction Algorithm Requiring No. Contextual Factors. IEICE. Jun. 1995;E78:662-668.
Takami et al., Automatic Generation of Hidden Markov Networks by a Successive State Splitting Algoritm. IEICE. 1993;J76:2155-2164.
Thompson et al., CLUSTAL W: improving the sensitivity of progressive multiple sequence alignment through sequence weighting, position-specific gap penalties and weight matrix choice. Nucleic Acids Res. Nov. 11, 1994;22(22):4673-80.
Timp et al., DNA base-calling from a nanopore using a Viterbi algorithm. Biophys J. May 16, 2012;102(10):L37-9. doi:10.1016/j. bpj.2012.04.009. Epub May 15, 2012.
United States District Court for the District of Delaware Order. *Pacific Biosciences of California, Inc. v. Oxford Nanopore Technolgoies, Inc.* Civil Action No. 17-275-RGA. Nov. 9, 2017.

(56) References Cited

OTHER PUBLICATIONS

United States Patent and Trademark Office. *Oxford Nanopore Technologies Inc*. Petition v *Pacific Biosciences of California, Inc*. for U.S. Pat. No. 9,546,400. Inter Partes Review of claims 1-15. 81 pages. Mar. 15, 2018.
Warren et al., Assembling millions of short DNA sequences using SSAKE. Bioinformatics. Feb. 15, 2007;23(4):500-1. Epub Dec. 8, 2006.
Winters-Hilt et al., A novel, fast, HMM-with-Duration implementation—for application with a new, pattern recognition informed, nanopore detector. BMC Bioinformatics. Nov. 1, 2007;8 Suppl 7:S19.
Winters-Hilt et al., Highly accurate classification of Watson-Crick basepairs on termini of single DNA molecules. Biophys J. Feb. 2003;84(2 Pt 1):967-76.
Winters-Hilt, Machine learning methods for channel current cheminformatics, biophysical analysis, and bioinformatics. University of California Santa Cruz. Mar. 2003. Dissertation. 176 pages.
Zeng et al., PyroHMMvar: a sensitive and accurate method to call short indels and SNPs for Ion Torrent and 454 data. Bioinformatics. Nov. 15, 2013;29(22):2859-68. doi: 10.1093/bioinformatics/btt512. Epub Aug. 31, 2013.
Zerbino et al., Velvet: algorithms for de novo short read assembly using de Bruijn graphs. Genome Res. May 2008;18(5):821-9. doi: 10.1101/gr.074492.107. Epub Mar. 18, 2008.
Zhu et al., Bayesian adaptive sequence alignment algorithms. Bioinformatics. 1998;14(1):25-39.

Branton et al., The potential and challenges of nanopore sequencing. Nat Biotechnol. Oct. 2008;26(10):1146-53. doi: 10.1038/nbt.1495.
Cabello-Aguilar et al., Experimental and simulation studies of unusual current blockade induced by translocation of small oxidized PEG through a single nanopore. Phys Chem Chem Phys. Sep. 7, 2014;16(33):17883-92. doi: 10.1039/c4cp01954g.
Chu et al., Real-time monitoring of DNA polymerase function and stepwise single-nucleotide DNA strand translocation through a protein nanopore. Angew Chem Int Ed Engl. Dec. 27, 2010;49(52):10106-9. doi: 10.1002/anie.201005460.
Fennouri et al., Single molecule detection of glycosaminoglycan hyaluronic acid oligosaccharides and depolymerization enzyme activity using a protein nanopore. ACS Nano. Nov. 27, 2012;6(11):9672-8. doi: 10.1021/nn3031047. Epub Oct. 17, 2012.
Hornblower et al., Single-molecule analysis of DNA-protein complexes using nanopores. Nat Methods. Apr. 2007;4(4):315-7. doi: 10.1038/nmeth1021. Epub Mar. 4, 2007.
Howorka et al., Nanopore analytics: sensing of single molecules. Chem Soc Rev. Aug. 2009;38(8):2360-84. doi: 10.1039/b813796j. Epub Jun. 15, 2009.
Muzard et al., DNA translocation and unzipping through a nanopore: some geometrical effects. Biophys J. May 19, 2010;98(10):2170-8. doi: 10.1016/j.bpj.2010.01.041.
Panwar et al., Enzyme-modulated DNA translocation through a nanopore. J Am Chem Soc. Dec. 30, 2009;131(51):18563-70. doi: 10.1021/ja904047q.
Stanke et al., Gene prediction with a hidden Markov model and a new intron submodel. Bioinformatics. Oct. 2003;19 Suppl 2:ii215-25. doi: 10.1093/bioinformatics/btg1080.

\* cited by examiner

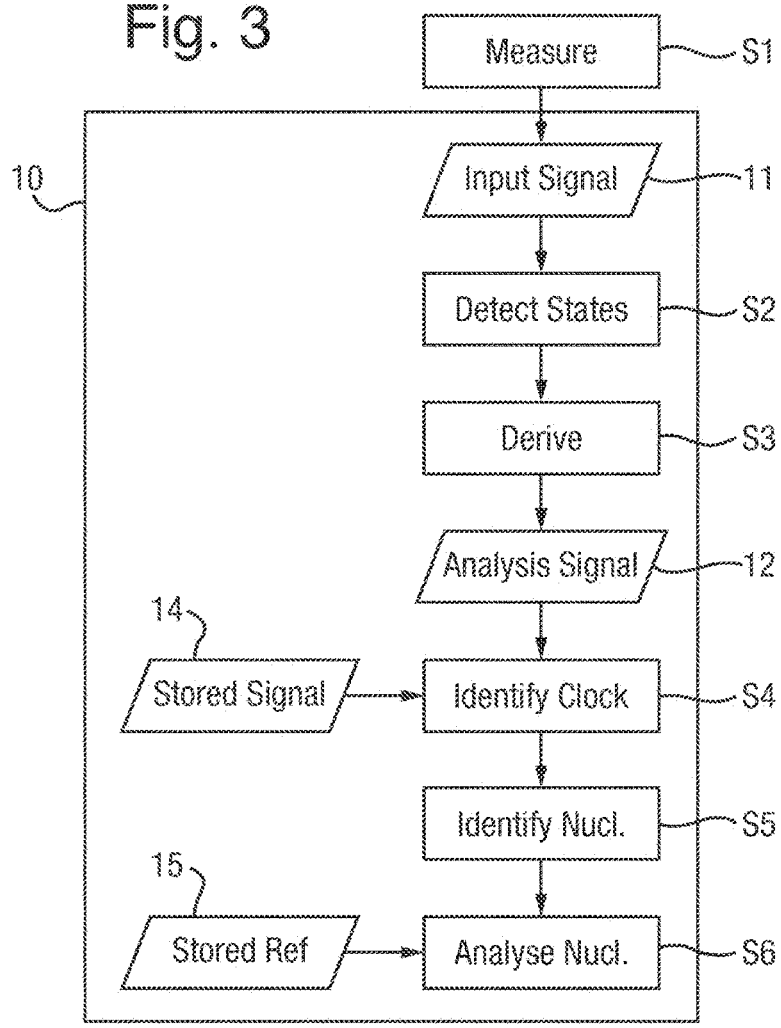
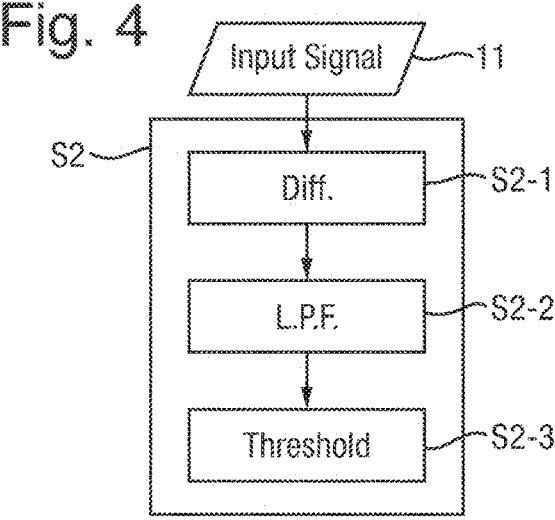

Fig. 5

CCCCCCCCCCCCCCCCCCCCCACCCCCCCCCCTTTGGATGACTACTTTGGATGAGTACATTGGAGTACATTGAAGTACATTGAAATCAGATCTACTATCGCATTCGATTCGATTCGCATTCGATGCAGGTCGTAGC (SEQ ID NO:5)
AAACCTACACTGAAACCTACACTGAAACCTACACTGATAGTCAGTTCAGTTAGTCAGTTAGTCAGTTAGTCAGTGTAAGAGTACTAAGAGTACTAAGAGTACTTCAGCATCG (SEQ ID NO:6)

41  42  43
    A A A
44

SEQUENCE LISTING

```
<160> NUMBER OF SEQ ID NOS: 27

<210> SEQ ID NO 1
<211> LENGTH: 111
<212> TYPE: DNA
<213> ORGANISM: Artificial Sequence
<220> FEATURE:
<223> OTHER INFORMATION: synthetic nucleotide

<400> SEQUENCE: 1
cccccccccc ccacccccccc cccccacccc cccccccct ttggatgagc tttggatgag      60
ctttggatga gcattcagat ctcactatcg cattctcatg caggtcgtag c              111

<210> SEQ ID NO 2
<211> LENGTH: 111
<212> TYPE: DNA
<213> ORGANISM: Artificial Sequence
<220> FEATURE:
<223> OTHER INFORMATION: synthetic nucleotide

<400> SEQUENCE: 2
gctacgacct gcatgagaat gcgatagtga gatctgaatg ctcatccaaa gctcatccaa      60
```
agctcatcca aagggggggg gggggtgggg ggggggggtg ggggggggggg g      111

<210> SEQ ID NO 3
<211> LENGTH: 111
<212> TYPE: DNA
<213> ORGANISM: Artificial Sequence
<220> FEATURE:
<223> OTHER INFORMATION: synthetic nucleotide

<400> SEQUENCE: 3
cccccccccc ccacccccccc cccccacccc ccccccccct ttggatgttc tttggatgtt      60
ctttggatgt tcattcagat ctcactatcg cattctcatg caggtcgtag c      111

<210> SEQ ID NO 4
<211> LENGTH: 61
<212> TYPE: DNA
<213> ORGANISM: Artificial Sequence
<220> FEATURE:
<223> OTHER INFORMATION: synthetic nucleotide

<400> SEQUENCE: 4
gctacgacct gcatgagaat gcgatagtga gatctgaatg ctcatccaaa gctcatccaa      60
a      61

<210> SEQ ID NO 5
<211> LENGTH: 111
<212> TYPE: DNA
<213> ORGANISM: Artificial Sequence
<220> FEATURE:
<223> OTHER INFORMATION: synthetic nucleotide

<400> SEQUENCE: 5
cccccccccc ccacccccccc cccccacccc ccccccccct ttggatgtac tttggatgta      60
ctttggatgt acattcagat ctcactatcg cattctcatg caggtcgtag c      111

<210> SEQ ID NO 6
<211> LENGTH: 61
<212> TYPE: DNA
<213> ORGANISM: Artificial Sequence
<220> FEATURE:
<223> OTHER INFORMATION: synthetic nucleotide

<400> SEQUENCE: 6
gctacgacct gcatgagaat gcgatagtga gatctgaatg tacatccaaa gtacatccaa      60
a      61

<210> SEQ ID NO 7
<211> LENGTH: 111
<212> TYPE: DNA
<213> ORGANISM: Artificial Sequence
<220> FEATURE:
<223> OTHER INFORMATION: synthetic nucleotide

<400> SEQUENCE: 7
cccccccccc ccacccccccc cccccacccc ccccccccct ttggatgtcc tttggatgtc      60
ctttggatgt ccattcagat ctcactatcg cattctcatg caggtcgtag c      111

<210> SEQ ID NO 8
<211> LENGTH: 61
<212> TYPE: DNA
<213> ORGANISM: Artificial Sequence
<220> FEATURE:

<223> OTHER INFORMATION: synthetic nucleotide

<400> SEQUENCE: 8
gctacgacct gcatgagaat gcgatagtga gatctgaatg gacatccaaa ggacatccaa    60
a    61

<210> SEQ ID NO 9
<211> LENGTH: 111
<212> TYPE: DNA
<213> ORGANISM: Artificial Sequence
<220> FEATURE:
<223> OTHER INFORMATION: synthetic nucleotide

<400> SEQUENCE: 9
cccccccccc caccccccc cccccacccc cccccccct tggatgctc tttggatgct    60 ctttggatgc tcattcagat ctcactatcg cattctcatg caggtcgtag c    111

<210> SEQ ID NO 10
<211> LENGTH: 61
<212> TYPE: DNA
<213> ORGANISM: Artificial Sequence
<220> FEATURE:
<223> OTHER INFORMATION: synthetic nucleotide

<400> SEQUENCE: 10
gctacgacct gcatgagaat gcgatagtga gatctgaatg agcatccaaa gagcatccaa    60
a    61

<210> SEQ ID NO 11
<211> LENGTH: 188
<212> TYPE: DNA
<213> ORGANISM: Artificial Sequence
<220> FEATURE:
<223> OTHER INFORMATION: synthetic nucleotide

<400> SEQUENCE: 11
cccccccccc caccccccc cccccacccc cccccccct tggatgagc tttggatgtc    60 ctttggatgc tctttggatg tactttggat gctctttgga tgctctttgg atgagctttg    120
gatgtacttt ggatgtcctt tggatgctcc ctttgatctc actatcgcat tctcatgcag    180
gtcgtagc    188

<210> SEQ ID NO 12
<211> LENGTH: 138
<212> TYPE: DNA
<213> ORGANISM: Artificial Sequence
<220> FEATURE:
<223> OTHER INFORMATION: synthetic nucleotide

<400> SEQUENCE: 12
gctacgacct gcatgagaat gcgatagtga gatcaaaggg agcatccaaa ggacatccaa    60
agtacatcca aagctcatcc aaagagcatc caaagagcat ccaaagtaca tccaaagagc    120
atccaaagga catccaaa    138

<210> SEQ ID NO 13
<211> LENGTH: 188
<212> TYPE: DNA
<213> ORGANISM: Artificial Sequence
<220> FEATURE:
<223> OTHER INFORMATION: synthetic nucleotide

<400> SEQUENCE: 13

```
cccccccccc caccccccc cccccacccc ccccccccct ttggatgctc tttggatgta      60
ctttggatgt actttggatg agctttggat gagctttgga tgtcctttgg atgtcctttg    120
gatgctcttt ggatgctctt tggatgtacc ctttgatctc actatcgcat tctcatgcag    180
gtcgtagc                                                             188
```

<210> SEQ ID NO 14
<211> LENGTH: 138
<212> TYPE: DNA
<213> ORGANISM: Artificial Sequence
<220> FEATURE:
<223> OTHER INFORMATION: synthetic nucleotide

<400> SEQUENCE: 14

```
gctacgacct gcatgagaat gcgatagtga gatcaaaggg tacatccaaa gagcatccaa     60
agagcatcca aaggacatcc aaaggacatc caaagctcat ccaaagctca tccaaagtac    120
atccaaagta catccaaa                                                  138
```

<210> SEQ ID NO 15
<211> LENGTH: 188
<212> TYPE: DNA
<213> ORGANISM: Artificial Sequence
<220> FEATURE:
<223> OTHER INFORMATION: synthetic nucleotide

<400> SEQUENCE: 15

```
cccccccccc caccccccc cccccacccc ccccccccct ttggatgtcc tttggatgta      60
ctttggatgc tctttggatg agctttggat gctctttgga tgtcctttgg atgagctttg    120
gatgtacttt ggatgtcctt tggatgtccc ctttgatctc actatcgcat tctcatgcag    180
gtcgtagc                                                             188
```

<210> SEQ ID NO 16
<211> LENGTH: 138
<212> TYPE: DNA
<213> ORGANISM: Artificial Sequence
<220> FEATURE:
<223> OTHER INFORMATION: synthetic nucleotide

<400> SEQUENCE: 16

```
gctacgacct gcatgagaat gcgatagtga gatcaaaggg gacatccaaa ggacatccaa     60
agtacatcca aagctcatcc aaaggacatc caaagagcat ccaaagctca tccaaagagc    120
atccaaagta catccaaa                                                  138
```

<210> SEQ ID NO 17
<211> LENGTH: 11
<212> TYPE: DNA
<213> ORGANISM: Artificial Sequence
<220> FEATURE:
<223> OTHER INFORMATION: synthetic nucleotide

<400> SEQUENCE: 17

```
ctttggatga g                                                          11
```

<210> SEQ ID NO 18
<211> LENGTH: 11
<212> TYPE: DNA
<213> ORGANISM: Artificial Sequence
<220> FEATURE:
<223> OTHER INFORMATION: synthetic nucleotide

```
<400> SEQUENCE: 18
ctttggatgt t                                                          11

<210> SEQ ID NO 19
<211> LENGTH: 11
<212> TYPE: DNA
<213> ORGANISM: Artificial Sequence
<220> FEATURE:
<223> OTHER INFORMATION: synthetic nucleotide

<400> SEQUENCE: 19
ctttggatgt a                                                          11

<210> SEQ ID NO 20
<211> LENGTH: 11
<212> TYPE: DNA
<213> ORGANISM: Artificial Sequence
<220> FEATURE:
<223> OTHER INFORMATION: synthetic nucleotide

<400> SEQUENCE: 20
ctttggatgt c                                                          11

<210> SEQ ID NO 21
<211> LENGTH: 33
<212> TYPE: DNA
<213> ORGANISM: Artificial Sequence
<220> FEATURE:
<223> OTHER INFORMATION: synthetic nucleotide

<400> SEQUENCE: 21
ctttggatgt cctttggatg tcctttggat gtc                                  33

<210> SEQ ID NO 22
<211> LENGTH: 38
<212> TYPE: DNA
<213> ORGANISM: Artificial Sequence
<220> FEATURE:
<223> OTHER INFORMATION: synthetic nucleotide

<400> SEQUENCE: 22
cccccccccc ccaccccccc ccccaccccc ccccccc                              38

<210> SEQ ID NO 23
<211> LENGTH: 40
<212> TYPE: DNA
<213> ORGANISM: Artificial Sequence
<220> FEATURE:
<223> OTHER INFORMATION: synthetic nucleotide

<400> SEQUENCE: 23
cattcagatc tcactatcgc attctcatgc aggtcgtagc                           40

<210> SEQ ID NO 24
<211> LENGTH: 11
<212> TYPE: DNA
<213> ORGANISM: Artificial Sequence
<220> FEATURE:
<223> OTHER INFORMATION: synthetic nucleotide

<400> SEQUENCE: 24
ctttggatgc t                                                          11

<210> SEQ ID NO 25
<211> LENGTH: 10
```

```
<212> TYPE: DNA
<213> ORGANISM: Artificial Sequence
<220> FEATURE:
<223> OTHER INFORMATION: synthetic nucleotide

<400> SEQUENCE: 25
catgtcgacc                                                              10

<210> SEQ ID NO 26
<211> LENGTH: 10
<212> TYPE: DNA
<213> ORGANISM: Artificial Sequence
<220> FEATURE:
<223> OTHER INFORMATION: synthetic nucleotide

<400> SEQUENCE: 26
gctattgact                                                              10

<210> SEQ ID NO 27
<211> LENGTH: 10
<212> TYPE: DNA
<213> ORGANISM: Artificial Sequence
<220> FEATURE:
<223> OTHER INFORMATION: synthetic nucleotide

<400> SEQUENCE: 27
taaggcctta                                                              10
```

ANALYSIS OF A POLYNUCLEOTIDE VIA A NANOPORE SYSTEM

RELATED APPLICATIONS

This application is a continuation of U.S. application Ser. No. 16/162,848, filed Oct. 17, 2018, which is a continuation of U.S. application Ser. No. 14/653,656, filed Jun. 18, 2015, which is a national stage filing under 35 U.S.C. § 371 of International Application No. PCT/GB2013/053359, filed Dec. 19, 2013, and foreign priority benefits are claimed under 35 U.S.C. § 119 (a)-(d) or 35 U.S.C. § 365 (b) of British application number 1222928.2, filed Dec. 19, 2012, the entire contents of each of which applications are incorporated herein by reference for all purposes.

REFERENCE TO AN ELECTRONIC SEQUENCE LISTING

The contents of the electronic sequence listing (0036670002US02-SEQ-KZM.txt; Size: 7,558 bytes; and Date of Creation: Jul. 7, 2021) is herein incorporated by reference in its entirety.

BACKGROUND

The present invention relates generally to the field of analysing a polynucleotide comprising nucleotides by making electrical measurements during translocation through a nanopore.

Nanopores represent an attractive way to analyse polynucleotides, for example to determine the identity of the polynucleotide or to estimate the identity of individual nucleotides in the polynucleotide for sequencing purposes. This is because the method is label-free, provides measurements dependent on small numbers or even single molecules, and generates an electric signal that is highly scalable.

In a measurement system utilising a nanopore, some property of the system depends on the nucleotides in the nanopore, and electrical measurements of that property are taken. For example, a measurement system be created by placing a nanopore in an insulating membrane and measuring voltage-driven ion flow through the nanopore in the presence of nucleotides of the polynucleotide. Depending on the nature of the nanopore, information about the nucleotides may be revealed by distinctive ion current signatures, such as the duration and extent of current block and the variance of current levels. Such types of measurement system using a nanopore has considerable promise, particularly in the field of sequencing a polynucleotide such as DNA or RNA, and has been the subject of much recent development.

There is currently a need for rapid and cheap nucleic acid (e.g. DNA or RNA) sequencing technologies across a wide range of applications. Existing technologies are slow and expensive mainly because they rely on amplification techniques to produce large volumes of nucleic acid and require a high quantity of specialist fluorescent chemicals for signal detection. Nanopore sensing has the potential to provide rapid and cheap nucleic acid sequencing by reducing the quantity of nucleotide and reagents required.

Recent progress in the field can be split into two main categories, namely improvement to the nucleotide discrimination of the nanopore and control of the translocation of the polynucleotide through the nanopore.

Regarding nucleotide discrimination, recognition of nucleotide has been demonstrated for immobilised DNA strand using either alpha-Hemolysin (HL) as disclosed in Stoddart et al., Nano Lett. 2010 Sep. 8; 10 (9): 3633-7 [Reference 1], or *Mycobacterium smegmatis* porin A (MspA) as disclosed in Derrington et al., Proc Natl Acad Sci USA. 2010 Sep. 14; 107 (37): 16060-5 [Reference 2]. In these studies, the strands were held static in the nanopore either by attachment to streptavidin in the case of Reference 1 or by hybridising a piece of DNA to the DNA strand being read to the nanopore, thus providing a break when the dsDNA is lodged into the nanopore in the case of Reference 2.

Regarding control of translocation, a DNA polymerase enzyme (DNAP) has been used to control the translocation of DNA through a nanopore as disclosed in Lieberman et al., J Am Chem Soc. 2010 Dec. 22; 132 (50): 17961-72 [Reference 3]. This is attractive as provides the potential for the nucleotides to be read individually as they move through the nanopore. The combination of using Phi29 DNAP to control strand motion, together with MspA mutants for improved discrimination has recently been disclosed in WO-2012/107778.

For the published nanopore constructs, it has been shown that more than one nucleotide contributes to an observed current signal when the DNA is present in the nanopore. Although the current levels have been shown to be sequence dependent, the relationship between the recorded current and the nucleotide sequence is not known at this time. In addition, the enzyme-assisted movement of the DNA strand through the nanopore is not perfect, resulting in missed states.

It is typical of many types of measurement system, including the majority of currently known biological nanopores, that the value of each electrical measurement is dependent on a k-mer (being a group of k consecutive nucleotides), where k is a plural integer. This is because more than one nucleotide contributes to the observed signal. The phenomenon might be thought of conceptually as the measurement system having a "blunt reader head" that is bigger than the nucleotide being measured. In such a situation, the number of different k-mers to be resolved increases to the power of k. For example, if there are n possible nucleotides, the number of different k-mers to be resolved is $n^k$. While it is desirable to have clear separation between measurements for different k-mers, it is common for some of these measurements to overlap. Especially with high numbers of nucleotides in the k-mer, i.e. high values of k, it can become difficult to resolve the measurements produced by different k-mers, to the detriment of deriving information about the polynucleotide, for example an estimate of the underlying sequence of nucleotides.

There are a number of ways that the methods could be developed to obtain sequence information.

One approach is to modify the nanopore of the measurement system. Much research has aimed at design of a measurement system that provides resolvable measurements that are dependent on a single nucleotide but this has proved difficult in practice, due to variation in electrical measurements that can arise to varying extents from inherent variation in the underlying physical or biological system and/or measurement noise that is inevitable due the small magnitude of the properties being measured. Other work has accepted measurements that are dependent on k-mers, but has aimed at design of a measurement system in which the measurements from different k-mers are resolvable from each other. However, practical limitations mean again that this is very difficult since distributions of signals produced by some different k-mers can often overlap.

Another approach is to improve the analytical techniques that obtain useful information from the measurements. For example, International Patent Appl. No. PCT/GB2012/052343 discloses estimation of sequences of nucleotides using particular analytical techniques taking account of a model, based on the likelihood predicted by the model of the actual series of measurements being produced In the more general field of DNA sequencing using a range of sequencing techniques including PCR (polymerase chain reaction) techniques, WO-00/393333 proposes a magnification technique in which a target polynucleotide is pre-processed to improve the discrimination of the sequencing technique employed. In particular, there is proposed that the pre-processing causes magnifying tags to be associated with bases in the target nucleotide. In one approach, the magnifying tags are adapter molecules attached to a form of the target sequence adapted for binding of the adapter molecules. WO-00/393333 proposes the application of the magnification technique to a wide range of sequencing techniques. These mostly do not using nanopores but in one example the target polynucleotide is converted into a binary code consisting of purine and pyrimidine signals and electrical measurements taken during translocation through a nanopore are used to discriminate the purines and pyrimidines of the binary code.

SUMMARY OF THE INVENTION

According to a first aspect of the present invention, there is provided a method of analysing a target polynucleotide, the method using an expanded polynucleotide derived from the target polynucleotide, the expanded polynucleotide comprising, in respect of each nucleotide in the target polynucleotide in order, clock nucleotides and at least one signal nucleotide in a predetermined order, the clock nucleotides having a predetermined sequence common to each nucleotide in the target polynucleotide, and the at least one signal nucleotide that is characteristic of the identity of the respective nucleotide in the target polynucleotide, the method comprising, during translocation of the expanded polynucleotide through a nanopore, making electrical measurements dependent on the nucleotides within the nanopore and deriving an analysis signal therefrom.

Accordingly, the present method is directed to analysis that involves making electrical measurements during translocation of a polynucleotide through a nanopore. However, in order to provide information about a target polynucleotide, the method uses an expanded polynucleotide derived from that target polynucleotide. Thus, the electrical measurements are made during translocation of the expanded polynucleotide through a nanopore. Thus, the electrical measurements are dependent on the expanded polynucleotide. An analysis signal is derived from the electrical measurements.

In particular, the expanded polynucleotide comprises clock nucleotides and at least one signal nucleotide in respect of each nucleotide in the target polynucleotide. The order of the nucleotides in the target polynucleotide is preserved. That is, the expanded units comprising clock nucleotides and at least one signal nucleotide in respect of successive nucleotides in the target polynucleotide are in the same order as the respective nucleotides in the target polynucleotide. Further, the clock nucleotides and at least one signal nucleotide in respect of each nucleotide in the target polynucleotide are in a predetermined order.

The clock nucleotides have a predetermined sequence that is common to each nucleotide in the target polynucleotide. On the other hand, the at least one signal nucleotide is characteristic of the identity of the respective nucleotide in the target polynucleotide.

The use of an expanded polynucleotide in this form provides significant advantages in the analysis of the target polynucleotide. In particular, the analysis signal will include clock signals derived from at least one of the clock nucleotides in respect of each nucleotide in the target polynucleotide. The analysis signal will further include nucleotide signals derived from the at least one signal nucleotide in respect of each nucleotide in the target polynucleotide. A clock or nucleotide signal may be derived entirely from respectively the clock nucleotides or the signal nucleotides, respectively. Depending upon the number of nucleotides within the nanopore that contribute to an observed signal, the clock signals may be derived additionally from one or more of the signal nucleotides and/or the nucleotide signals may be derived additionally from one or more of the signal nucleotides.

As a result of the clock nucleotides having a predetermined sequence common to each nucleotide in the target polynucleotide, a clock signal associated with a particular nucleotide of the target polynucleotide may be derived from that common sequence. As a result, it becomes possible during analysis of the analysis signal to identify such clock signals reliably within overall analysis signal. The main purpose of the clock signal is not to provide information about the target polynucleotide but to signal translocation through the nanopore past the "reader head", that is the location where nucleotides affect the measurement signal.

The clock signals effectively parses the analysis signal allowing the nucleotide signals to be identified relative to the positions of the identified clock signals, even though the nucleotide signals themselves vary unpredictably in dependence on the at least one signal nucleotide from which they derive. Once the nucleotide signals have been identified in this way, they may be analysed to analyse the target polynucleotide, because each nucleotide signal is derived from the at least one signal nucleotide in respect of a different nucleotide in the target polynucleotide. The nucleotide signals may be analysed to determine the identity of individual nucleotides in the target polynucleotide. The nucleotide signals may be analysed to determine the target polynucleotide or one or more regions thereof. The one or more regions of the polynucleotide may be a particular group or groups of nucleotides, for example whose presence is indicative of a prevalence towards a particular condition or disease state.

In general, expanding the sequence of the polynucleotide reduces the number of nucleotides of the target polynucleotide that would contribute to the observed signal which is advantageous. Depending upon the number of nucleotides within the nanopore that contribute to an observed signal and the extent to which the polynucleotide is expanded, only a single nucleotide of the target polynucleotide may contribute to a particular measurement signal.

In this way, the clock signals improve the analysis of the target polynucleotide since the identification of nucleotide signals corresponding to different nucleotides in the target polynucleotide is more reliable compared to a direct measurement of the target polynucleotide.

In the case that the expanded polynucleotide was derived from the target polynucleotide using a technique employing a restriction enzyme, then the predetermined sequence of the clock nucleotides may comprise a restriction site for a restriction enzyme. This may occur inherently due to the preparation technique used to derive the expanded polynucleotide.

In this case, advantageously the predetermined sequence of the clock nucleotides may further comprise at least one further nucleotide. This extends the predetermined sequence as compared to the restriction site and provides a number of advantages in assisting the identification of the clock signal derived from the clock nucleotides.

Firstly, the at least one further nucleotide increases the length of the clock sequence and hence of the clock signal. This increase in length in itself makes the clock signals easier to identify.

Secondly, the at least one further nucleotide may be selected to provide a clock signal providing relatively good discrimination. For any given measurement system, the signals derived from some sequences may be more easily discriminated from the set of possible signals than the signals derived from other sequences. This is particularly the case that the electrical measurements are dependent on a k-mer, were k is greater than one. Whereas the restriction site is limited by the choice of restriction enzyme, the at least one further nucleotide can be chosen by design. Thus, the at least one further nucleotide is chosen to provide sufficient discrimination. In general, the at least one further nucleotide may comprise any number of one or more nucleotides.

In accordance with a second aspect of the present invention, there is provided a preparation method of expanding a target polynucleotide, the method comprising expanding each nucleotide in the target polynucleotide in order into clock nucleotides and at least one signal nucleotide in a predetermined order by a technique employing a restriction enzyme, wherein the clock nucleotides have a predetermined sequence common to each nucleotide in the target polynucleotide and comprising a plurality of nucleotides that is a restriction site for the restriction enzyme and at least one further nucleotide, and the at least one signal nucleotide that is characteristic of the identity of the respective nucleotide in the target polynucleotide.

This preparation method provides an expanded polynucleotide that comprises the at least one further nucleotide and provides the advantages thereof when used in a method of analysing a target polynucleotide in accordance with the first aspect of the present invention.

The choice of the length and sequence identity of the at least one further nucleotide may depend on the measurement system being used. In assessing the degree of discrimination provided, regard may be had to the clock signal derived from the at least one further nucleotide alone or to the clock signal derived from the at least one further nucleotide in combination with the restriction site.

In some expanded polynucleotides, the at least one signal nucleotide that is characteristic of the identity of a respective nucleotide in the target polynucleotide may consist of a single signal nucleotide. In that case, the single signal nucleotide may have the same identity as the respective nucleotide in the target polynucleotide, or may have a different identity, for example being the compliment of the nucleotide in the target polynucleotide.

In the case of using a single signal nucleotide in respect of each nucleotide of the target molecule, discrimination may be improved even though there has been no expansion in the part of the expanded polynucleotide that is characteristic of the target polynucleotide. In the case that the electrical measurements are dependent on a k-mer where k is greater than one, electrical measurements are dependent on the single signal nucleotide in combination with one or more clock nucleotides adjacent the single signal nucleotide. These clock nucleotides have an identity which both is known and is common for each signal nucleotide. As compared to the case of deriving measurements from the target nucleotide itself wherein each measurement is dependent on a k-mer in which the identity of each nucleotide of the k-mer is variable and a priori unknown, this reduces the number of possible k-mers including the signal nucleotide that need to be discriminated and hence makes it easier to identify the actual identity of the nucleotide of the target molecule from the nucleotide signal.

In other expanded polynucleotides, the at least one signal nucleotide that is characteristic of the identity of a respective nucleotide in the target polynucleotide may consist of plural signal nucleotides having a sequence that is characteristic of the identity of the nucleotide in the target polynucleotide. In this case, one of the plural signal nucleotides may have the same identity as the respective nucleotide in the target polynucleotide, but that is not essential.

In the case of using plural signal nucleotides in respect of each nucleotide of the target molecule, discrimination may be improved. As well as achieving a similar advantage as discussed above in respect of a single signal nucleotide, the improvement in discrimination occurs because the part of the expanded polynucleotide that is characteristic of the target polynucleotide has been expanded. The number of possible sequences of the plural signal nucleotides, each being characteristic of a different possible nucleotide, is reduced compared to the possible sequences of an arbitrary sequence of the same length. Effectively, the length of the nucleotide signal is increased but the number of possible nucleotide signals to be discriminated remains the same. This increases the distinction between the nucleotide signals corresponding to different nucleotide in the target polynucleotides, making it easier to discriminate between them.

Due to the fact that many of the nucleotides of the expanded polynucleotide are predetermined, the measurement signal compared to one obtained from an unexpanded target nucleotide is much easier to analyse. Consequently it is possible using this technique to employ a wider range of nanopores than could not otherwise be employed. In particular it enables the use of nanopores, such as α-hemolysin, having very blunt reader-heads, namely where the observed signal is dependent upon a large number of nucleotides.

The clock nucleotides and plural signal nucleotides in a single expanded unit may be arranged in a predetermined order in which the plural signal nucleotides are contiguous. In this case, the plural signal nucleotides corresponding to an individual nucleotide in the target are all arranged between clock nucleotides, and so the nucleotide signal is derived solely from the region of the analysis signal between two clock signals. However, in principle this is not essential. Instead, the clock nucleotides and plural signal nucleotides in a single expanded unit may be arranged in a predetermined order in which the plural signal nucleotides are split by the clock nucleotides. In this case, the nucleotide signal is derived from regions of the analysis signal on both sides of a single clock signal. The method in accordance with the first aspect of the present invention may be performed on a target polynucleotide that has already been prepared, or alternatively may additionally comprise a preparation step, performed before the step of making measurements, expanding the target polynucleotide to form the expanded polynucleotide.

The preparation of the expanded polynucleotide may be performed using any suitable technique.

One possible technique for preparation of the expanded polynucleotide is to use a restriction enzyme using techniques that are known in themselves. A specific example of such a technique using a restriction enzyme is described below.

BRIEF DESCRIPTION OF THE DRAWINGS

To allow better understanding, embodiments of the present invention will now be described by way of non-limitative example with reference to the accompanying drawings, in which:

FIG. 3 is a flowchart of a method of analyzing an input signal comprising measurements of a polymer;

FIG. 4 is a flowchart of a state detection step of FIG. 3;

FIG. 5 is a diagram of an example DNA strand used in an example (SEQ ID NO: 5 and SEQ ID NO: 6);

DETAILED DESCRIPTION OF THE INVENTION

Figure 1:
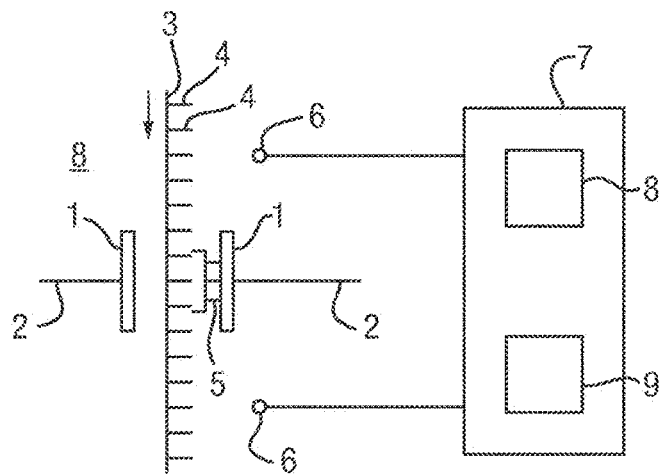
FIG. 1 is a schematic diagram of a measurement system comprising a nanopore.

This description makes reference to various sequences SEQ ID NO: 1 to 27, of which:
SEQ ID NO: 1 shows AU34 (GGG Set A, B);
SEQ ID NO: 2 shows AU35 (Complementary DNA for SEQ ID NO: 1);
SEQ ID NO: 3 shows AU42 (TTT Set A);
SEQ ID NO: 4 shows AU43 (Complementary DNA for SEQ ID NO: 3);
SEQ ID NO: 5 shows AU38 (AAA Set A, B);
SEQ ID NO: 6 shows AU39 (Complementary DNA for SEQ ID NO: 5);
SEQ ID NO: 7 shows AU46 (CCC Set A, B);
SEQ ID NO: 8 shows AU47 (Complementary DNA for SEQ ID NO: 7);
SEQ ID NO: 9 shows AU52 (TTT Set B);
SEQ ID NO: 10 shows AU53 (Complementary DNA for SEQ ID NO: 9);
SEQ ID NO: 11 shows AU76 (GCTATTGACT (SEQ ID NO: 26) Set B);
SEQ ID NO: 12 shows AU77 (Complementary DNA for SEQ ID NO: 11);
SEQ ID NO: 13 shows AU78 (TAAGGCCTTA (SEQ ID NO: 27) Set B);
SEQ ID NO: 14 shows AU79 (Complementary DNA for SEQ ID NO: 13);
SEQ ID NO: 15 shows AU80 (CATGTCGACC (SEQ ID NO: 25) Set B); and
SEQ ID NO: 16 shows AU81 (Complementary DNA for SEQ ID NO: 15).

The present invention is applicable to a range of polynucleotides, for example as follows.

The polynucleotide (or nucleic acid) is typically deoxyribonucleic acid (DNA), ribonucleic acid (RNA), cDNA or a synthetic nucleic acid known in the art, such as peptide nucleic acid (PNA), glycerol nucleic acid (GNA), threose nucleic acid (TNA), locked nucleic acid (LNA) or other synthetic polynucleotides with nucleotide side chains. The nucleic acid may be single-stranded, be double-stranded or comprise both single-stranded and double-stranded regions. Typically cDNA, RNA, GNA, TNA or LNA are single stranded.

The nucleotides may be of any type. The nucleotides can be naturally occurring or artificial. A nucleotide typically contains a nucleobase, a sugar and at least one phosphate group. The nucleobase is typically heterocyclic. Suitable nucleobases include purines and pyrimidines and more specifically adenine, guanine, thymine, uracil and cytosine. The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate or triphosphate.

The nucleotide can be a damaged or epigenetic base. The nucleotide can be labelled or modified to act as a marker with a distinct signal. This technique can be used to identify the absence of a base, for example, an abasic unit or spacer in the polynucleotide. The method could also be applied to any type of polynucleotide.

Of particular use when considering measurements of modified or damaged DNA (or similar systems) are the methods where complementary data are considered. The additional information provided allows distinction between a larger number of underlying states.

The present invention may be applied to a range of types of electrical measurements taken by a range of measurement systems, as discussed further below.

The measurement system is a nanopore system that comprises a nanopore. The electrical measurements are taken during translocation of the polynucleotide through the nanopore. The translocation of the polynucleotide through the nanopore generates a characteristic signal in the measured property that may be observed, and may be referred to overall as an "event".

The nanopore is a pore, typically having a size of the order of nanometres, that allows the passage of polynucleotides therethrough. A property that depends on the nucleotides translocating through the nanopore may be measured. The property may be associated with an interaction between the polynucleotide and the nanopore. Interaction of the polynucleotide may occur at a constricted region of the nanopore. The measurement system measures the property, producing a measurement that is dependent on the nucleotides of the polynucleotide. The electrical measurements may comprise measurements of ion flow through the nanopore.

The nanopore may be a biological pore or a solid state pore.

Where the nanopore is a biological pore, it may have the following properties.

The biological pore may be a transmembrane protein pore. A transmembrane protein pore is a polypeptide or a collection of polypeptides that permits hydrated ions to flow from one side of a membrane to the other side of the membrane. The transmembrane protein pore is capable of forming a pore that may permit hydrated ions driven by an applied potential to flow from one side of the membrane to the other. The transmembrane protein pore allows a polynucleotide to translate through the pore.

The transmembrane protein pore may be a monomer or an oligomer. The pore is may be made up of several repeating subunits, such as 6, 7 or 8 subunits. The pore is more preferably a heptameric or octameric pore.

The transmembrane protein pore typically comprises a barrel or channel through which the ions may flow. The subunits of the pore typically surround a central axis and contribute strands to a transmembrane β-barrel or channel or a transmembrane α-helix bundle or channel.

The barrel or channel of the transmembrane protein pore typically comprises amino acids that facilitate interaction with analyte, such as polymers, nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and polymers, nucleotides, polynucleotides or nucleic acids.

Transmembrane protein pores for use in accordance with the invention can be derived from β-barrel pores or α-helix bundle pores.

β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and α outer membrane proteins, such as WZA and ClyA toxin. The transmembrane pore may be derived from Msp or from α-hemolysin (α-HL).

The transmembrane protein pore may be derived from Msp, preferably from MspA such as disclosed by WO-2010/034018. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. The pore may also comprise one or more constructs that comprise two or more covalently attached monomers derived from Msp. Suitable pores are disclosed in WO-2012/107778. Preferably the pore is derived from MspA or a homolog or paralog thereof.

The biological pore may be a naturally occurring pore or may be a mutant pore. Typical pores are described in WO-2010/109197, Stoddart D et al., Proc Natl Acad Sci, 12; 106 (19): 7702-7, Stoddart D et al., Angew Chem Int Ed Engl. 2010; 49 (3): 556-9, Stoddart D et al., Nano Lett. 2010 Sep. 8; 10 (9): 3633-7, Butler T Z et al., Proc Natl Acad Sci 2008; 105 (52): 20647-52.

The biological pore may be M2MspA (D90N/D91N/D93ND118R/D134R/E139K) as disclosed by WO-2010/034018, herein referred to as MS-(B1)$_8$ (i.e. 8 identical B1 monomers). Pores can be produced using standard methods known in the art. The pore monomers may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB 10/000133 (published as WO 2010/086603). Methods for inserting pores into membranes are discussed.

The biological pore may be inserted into an amphiphilic layer such as a biological membrane, for example a lipid bilayer. An amphiphilic layer is a layer formed from amphiphilic molecules, such as phospholipids, which have both hydrophilic and lipophilic properties. The amphiphilic layer may be a monolayer or a bilayer. The amphiphilic layer may be a co-block polymer such as disclosed by (Gonzalez-Perez et al., Langmuir, 2009, 25, 10447-10450). Alternatively, a biological pore may be inserted into a solid state layer.

Alternatively, a nanopore may be a solid state pore comprising an aperture formed in a solid state layer.

A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from graphene. Suitable graphene layers are disclosed in WO 2009/035647 and WO-2011/046706.

A solid state pore is typically an aperture in a solid state layer. A solid state pore may be used in combination with additional components which provide an alternative or additional measurement of the polynucleotide such as tunnelling electrodes (for example as described in Ivanov A P et al., Nano Lett. 2011 Jan. 12; 11 (1): 279-85), or a field effect transistor (FET) device (for example as described in WO 2005/124888). Solid state pores may be formed by known processes including for example those described in WO 00/79257.

In one type of measurement system, the electrical measurements taken may be measurements of the ion current flowing through a nanopore. These and/or other electrical measurements may be made using standard single channel recording equipment as describe in Stoddart D et al., Proc Natl Acad Sci, 12; 106 (19): 7702-7, Lieberman K R et al, J Am Chem Soc. 2010; 132 (50): 17961-72, and WO-2000/28312. Alternatively, electrical measurements may be made using a multi-channel system, for example as described in WO-2009/077734 and WO-2011/067559.

The step of deriving an analysis signal may comprise detecting states in electrical measurements, and deriving, from each state, at least one value representing a characteristic of the state to form said analysis signal.

In some measurement systems, the event consisting of translocation of the polynucleotide through the nanopore may be performed in a ratcheted manner in which successive nucleotides are registered with the nanopore. In such a case, it is observed that the electrical measurements are arranged in groups where the measurement is generally constant (although subject to variances as discussed below). Each group of measurements may be referred to as a "state" in the measurements. Each group of measurements is associated with a step of the ratcheted movement. Each state in the measurements corresponds to a physical state in which the polynucleotide is in a respective position relative to the nanopore (although subject to the practical difficulty of identifying states in the measurements corresponding to different physical states providing similar electrical measurements). Although there may be variation in the precise position during the period of a state, there are large scale movements of the polynucleotide between the physical states. Depending on the nature of the measurement system, the states may occur as a result of a binding event in the nanopore.

In order to allow measurements to be taken as the polynucleotide translocates through a nanopore, the rate of translocation can be controlled by a polynucleotide binding moiety. Typically the moiety can move the polynucleotide through the nanopore with or against an applied field. The moiety can be a molecular motor using for example, in the case where the moiety is an enzyme, enzymatic activity, or as a molecular brake. There are a number of methods proposed for controlling the rate of translocation of a polynucleotide including use of polynucleotide binding enzymes. Suitable enzymes for controlling the rate of translocation of polynucleotides include, but are not limited to, polymerases, helicases, exonucleases, single stranded and double stranded binding proteins, and topoisomerases, such as gyrases. The polynucleotide interacting moiety may be any disclosed in WO-2010/086603, WO-2012/107778, or Lieberman K R et al, J Am Chem Soc. 2010; 132 (50): 17961-72, and for voltage gated schemes (for example as disclosed in Luan B et al., Phys Rev Lett. 2010; 104 (23): 238103).

The polynucleotide binding moiety can be used in a number of ways to control the polynucleotide motion. The moiety can move the polynucleotide through the nanopore with or against the applied field. The moiety can be used as a molecular motor using for example, in the case where the moiety is an enzyme, enzymatic activity, or as a molecular brake.

The translocation of the polynucleotide may be controlled by a molecular ratchet that controls the movement of the polynucleotide through the nanopore to be performed in a ratcheted manner.

The molecular ratchet may be a polynucleotide binding protein. For polynucleotides, the polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target polynucleotide and controlling its movement through the nanopore. For instance, the enzyme may be modified to remove its enzymatic activity or may be used under conditions which prevent it from acting as an enzyme. Such conditions are discussed in more detail below. The enzyme may be covalently attached to the nanopore as discussed above.

The polynucleotide handling enzyme may be derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in WO 2010/086603.

Preferred enzymes are polymerases, exonucleases, helicases and topoisomerases, such as gyrases and variants thereof. The enzyme may be derived from a Phi29 DNA polymerase (Phi29 DNAP). The variant may include modifications that facilitate binding of the polynucleotide and/or facilitate its activity at high salt concentrations and/or room temperature.

It has been observed that the use of some enzymes as molecular ratchets may result occasionally in occasionally a non step-wise motion of the nucleotides of the polynucleotide through the pore. For example, the enzyme disassociate itself from the polynucleotide causing the polynucleotide to slip or advance through the pore effectively resulting in a missed measurement in respect of a particular k-mer. A particular advantage of employing the expanded polynucleotide of the invention is that the chances of missing a measurement due to a non-stepwise motion of the nucleotides when used in conjunction with nanopores with very blunt reader heads, namely those whose measurement signal is dependent upon a k-mer where k may be 7, 8, 9, 10, 11, 12, 13, 14 or more.

An additional problem sometimes experienced when using some enzymes as molecular ratchets is that the polynucleotide can stall within the nanopore for a period of time that is typically longer than might be usually experienced. It can be difficult to distinguish between a stalled polynucleotide and a homopolymeric region, namely wherein the target polynucleotide has two or more of the same nucleotides in succession. An advantage of the present advantage is that expanding the polynucleotide sequence enables homopolymeric regions to be more easily determined.

The two strategies for single strand DNA sequencing are the translocation of the DNA through the nanopore, both cis to trans and trans to cis, either with or against an applied potential. The most advantageous mechanism for strand sequencing is the controlled translocation of single strand DNA through the nanopore under an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the nanopore in a controlled stepwise manner, trans to cis, against the applied potential. Alternatively, the single strand DNA dependent polymerases can act as molecular brake slowing down the movement of a polynucleotide through the nanopore. Any moieties, techniques or enzymes described in WO-2012/107778 or WO-2012/033524 could be used to control polynucleotide motion.

The methods may be carried out using an apparatus that is suitable for investigating a nanopore, typically involving a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed.

The methods may involve measuring the current passing through the pore during one or more interactions with the nucleotide(s). Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore during one or more interactions with the nucleotide. Suitable conditions for measuring ionic currents through transmembrane protein pores are known in the art and disclosed in the Example. The method is typically carried out with a voltage applied across the membrane and pore. The voltage used is typically from +2 V to −2 V, typically from −400 mV to +400 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. NaCl is preferred. The salt concentration may be at saturation. The salt concentration may be 3M or lower and is typically from 0.1 to 2.5 M. High salt concentrations provide a high signal to noise ratio and allow for currents indicative of the presence of a polymer to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0.

The methods may be carried out at from 0° C. to 100° C. The methods are typically carried out at room temperature and may be carried out at a temperature that optimally supports enzyme function, such as about 37° C.

The method is typically carried out in the presence of free nucleotides or free nucleotide analogues and an enzyme cofactor that facilitate the action of the molecular ratchet or enzyme. The free nucleotides may be one or more of any of the individual nucleotides discussed above. The free nucleotides include, but are not limited to, mono, di and triphosphates of adenosine, guanosine, thymidine, uridine, cytidine, deoxyadenosine, deoxyguanosine, deoxythymidine, deoxyuridine or deoxycytidine The free nucleotides are preferably adenosine triphosphate The enzyme cofactor is a factor that allows the enzyme to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The target polymer may be contacted with the molecular ratchet and the pore in any order. In is preferred that, when the target polymer is contacted with the molecular ratchet and the pore, the target polymer firstly forms a complex with the molecular ratchet. When the voltage is applied across the pore, the target polymer/molecular ratchet complex then forms a complex with the pore and controls the movement of the polymer through the pore.

However, alternative types of measurement system and electrical measurements are also possible. Some examples of alternative types of electrical measurement include without limitation: current measurements, impedance measurements, tunnelling measurements (for example as disclosed in Ivanov A P et al., Nano Lett. 2011 Jan. 12; 11 (1): 279-85), and FET measurements (for example as disclosed in WO2005/124888). Optical measurements may be combined with electrical measurements (Soni G V et al., Rev Sci Instrum. 2010 January; 81 (1):014301). The measurement may be a transmembrane current measurement such as measurement of ion current flow through a nanopore. The ion current may typically be the DC ion current, although in principle an alternative is to use the AC current flow (i.e. the magnitude of the AC current flowing under application of an AC voltage). The measurement system may comprise a plurality of pores. The apparatus preferably further comprise a plurality of a polymer ratchets. The apparatus may be any conventional apparatus for polymer analysis, such as an array or a chip.

The apparatus may comprises: a sensor device that is capable of supporting the membrane and plurality of pores and being operable to perform polymer characterising using the pores; at least one reservoir for holding material for performing the characterising; a fluidics system configured to controllably supply material from the at least one reservoir to the sensor device; and a plurality of containers for receiving respective samples, the fluidics system being configured to supply the samples selectively from the containers to the sensor device. The apparatus may be any of those described in WO-2008/102120, WO-2009/077734, WO 2010/122293, WO-2011/067559 or WO-00/28312, all of which are incorporated herein by reference.

The apparatus may be a diagnostic device. The diagnostic device may be a benchtop or handheld device. The device may be operated in conjunction with a cartridge, the cartridge comprising the nanopore assay components and for receiving the fluid sample. The cartridge may be housed in the device or otherwise operably connectable with the device. The cartridge may be subsequently removed or disconnected from the device in order to clean the cartridge for re-use, or for disposal. Thereafter an unused or cleaned cartridge may be used with the device. The cartridge may be an integral part of the device wherein the device is disposable after use. The cartridge will typically have a sample application region for receiving a fluid sample. The sample application region may be a microfluidic channel or a porous sample pad for example to directly receive a urine sample. The size of sample would typically range from 0.25 uL to 10 mL. The sample application region may serve to directly receive a sample from a patient, for example a sample of blood obtained with a fingerstick. The cartridge may comprise a red blood cell filter for filtering red blood cells. The cartridge may comprise dried reagents such as a salt, an anticoagulant, or a buffer. The device will typically comprise data input and output ports and a memory for sending or receiving and storing data, such as information in relation to feature vectors, patient ID, and measurement results. The device may have wireless connectivity for communicating with a remote server or medical professional. Typically the device and cartridge are not restricted to measurement of a particular analyte and may capable of measuring any particular analyte and feature vectors relating to a particular analyte of interest may be uploaded and stored in the memory.

Herein, the term 'k-mer' refers to a group of k-nucleotides, where k is a plural integer. Although ideally the measurements would be dependent on a single nucleotide, with many typical measurement systems, the measurement is dependent on a k-mer of the polynucleotide. That is, each measurement is dependent on the sequence of each of the nucleotides in a k-mer where k is a plural integer. Typically the measurements are of a property that is associated with an interaction between the polynucleotide and the measurement system.

In some measurement systems, the measurements are dependent on small groups of nucleotides, for example doublets or triplets of nucleotides (i.e. in which k=2 or k=3). In other measurement systems, advantage is obtained from measurements that are dependent on larger groups of nucleotides, i.e. with a "broad" resolution. Such broad resolution may be particularly useful for examining homopolynucleotide regions.

Especially where measurements are dependent on a k-mer, it is desirable that the measurements are resolvable (i.e. separated) for as many as possible of the possible k-mers. Typically this can be achieved if the measurements produced by different k-mers are well spread over the measurement range and/or have a narrow distribution. This may be achieved to varying extents by different measurement systems. However, it is a particular advantage of the present invention, that it is not essential for the measurements produced by different k-mers to be resolvable.

FIG. 1 schematically illustrates an example of a measurement system 10 comprising a nanopore that is a biological pore 1 inserted in a biological membrane 2 such as an amphiphilic layer. A polynucleotide 3 comprising a series of nucleotides 4 is translocated through the biological pore 1 as shown by the arrows. The polynucleotide 3 interacts with an active part 5 of the biological pore 1 causing an electrical property such as the trans-membrane current to vary in dependence on a k-mer inside the biological pore 1. In this example, the active part 5 is illustrated as interacting with a k-mer of three nucleotides 4, but this is not limitative.

Electrodes 6 arranged on each side of the biological membrane 2 are connected to a an electrical circuit 7, including a control circuit 8 and a measurement circuit 9.

The control circuit 8 is arranged to supply a voltage to the electrodes 6 for application across the biological pore 1.

The measurement circuit 9 is arranged to measure the electrical property to provide electrical measurements. Thus the measurements are dependent on the k-mer inside the biological pore 1. In this example, the measurement circuit 9 makes electrical measurements across the electrodes 6, for example measurements of ion current flow.

Figure 2:
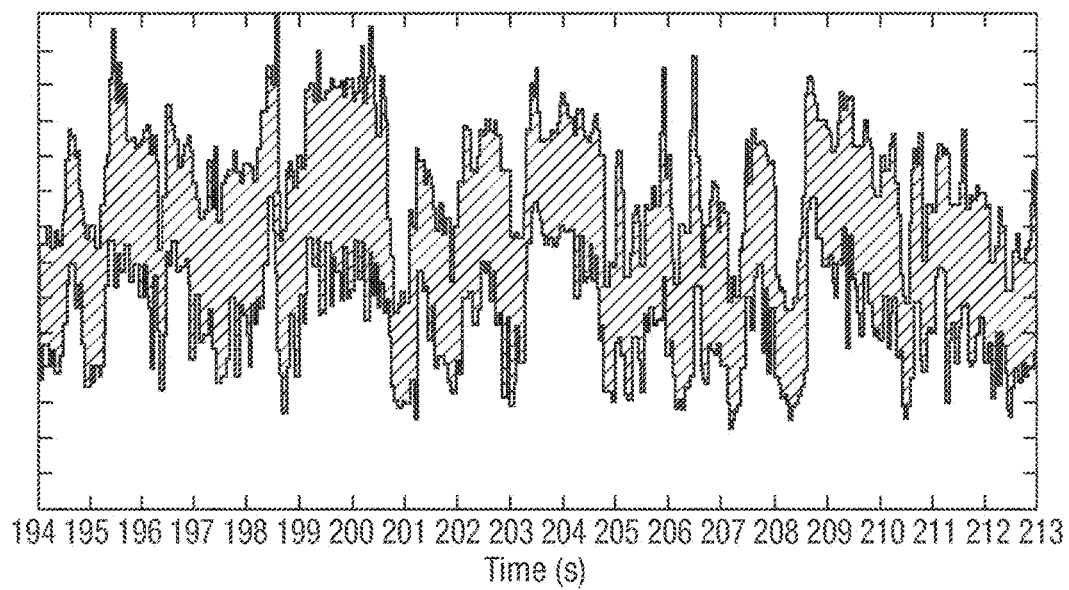
FIG. 2 is a plot of a signal of an event measured over time by a measurement system.

A typical type of signal comprising electrical measurements output by a measurement system is a "noisy step wave", although without limitation to this signal type. An example of an input signal having this form is shown in FIG. 2 for the case of an ion current measurement obtained using a measurement system comprising a nanopore. In this case, successive groups of plural electrical measurements are dependent on the same k-mer.

The plural measurements in each group are similar, subject to some variance discussed below, and therefore form a "state" in the electrical measurements, corresponding to a state of the measurement system in the manner discussed above. The signal moves between a set of states, which may be a large set. Given the sampling rate of the instrumentation and the noise on the signal, the transitions between states can be considered instantaneous, thus the signal can be approximated by an idealised step trace.

The measurements corresponding to each state are constant over the time scale of the event, but for most measurement systems will be subject to variance over a short time scale. Variance can result from measurement noise, for example arising from the electrical circuits and signal processing, notably from the amplifier in the particular case of electrophysiology. Such measurement noise is inevitable due the small magnitude of the properties being measured. Variance can also result from inherent variation or spread in the underlying physical or biological system of the measurement system. Most measurement systems will experience such inherent variation to greater or lesser extents. For any given measurement system, both sources of variation may contribute or one of these noise sources may be dominant.

In addition, typically there is no a priori knowledge of number of measurements in the group, which varies unpredictably.

These two factors of variance and lack of knowledge of the number of measurements can make it hard to distinguish some of the groups, for example where the group is short and/or the levels of the measurements of two successive groups are close to one another.

The signal takes this form as a result of the physical or biological processes occurring in the measurement system. Thus, each group of measurements may be referred to as a "state".

For example, in some measurement systems comprising a nanopore, the event consisting of translocation of the polynucleotide through the nanopore may occur in a ratcheted manner. During each step of the ratcheted movement, the ion current flowing through the nanopore at a given voltage across the nanopore is constant, subject to the variance discussed above. Thus, each group of measurements is associated with a step of the ratcheted movement. Each step corresponds to a state in which the polynucleotide is in a respective position relative to the nanopore. Although there may be some variation in the precise position during the period of a state, there are large scale movements of the polynucleotide between states. Depending on the nature of the measurement system, the states may occur as a result of a binding event in the nanopore.

The duration of individual states may be dependent upon a number of factors dependent on the measurement system, such as a potential applied across the nanopore, a type of enzyme used to ratchet the polynucleotide, whether the polynucleotide is being pushed or pulled through the nanopore by an enzyme, pH, salt concentration and a type of nucleoside triphosphate present. The duration of a state may vary typically between 0.5 ms and 3 s, depending on the measurement system, and, for any given nanopore system, having some random variation between states. The expected distribution of durations may be determined experimentally for any given measurement system.

There may be other information available either as part of the measurement or from additional sources that provides registration information. This other information may enable states to be identified.

The extent to which a given measurement system provides measurements that are dependent on k-mers and the size of the k-mers may be examined experimentally. For example, known polynucleotides may be synthesized and held at predetermined locations relative to the measurement system to investigate from the resultant measurements how the measurements depend on the identity of k-mers that interact with the measurement system.

One possible approach is to use a set of polynucleotides having identical sequences except for a k-mer at a predetermined position that varies for each polynucleotide of the set. The size and identity of the k-mers can be varied to investigate the effect on the measurements. Another possible approach is to use a set of polynucleotides in which the nucleotides outside a k-mer under investigation at a predetermined position vary for each polynucleotide of the set. This approach, or similar, can be applied to any measurement system enabling the location and a minimal k-mer description to be determined.

For typical measurement systems, it is often the case that measurements that are dependent on different k-mers are not all uniquely resolvable. For any given measurement system, it might or might not be possible to identify a function that transforms k measurements, that each depend in part on the same nucleotide, to obtain a single value that is resolved at the level of a nucleotide, or more generally the k-mer measurement is not describable by a set of parameters smaller than the number of k-mers.

There will now be described a specific analysis method that is shown in FIG. 3.

In step S1, the electrical measurements are made using a measurement system as described above.

A signal comprising the electrical measurements is input as an input signal 11 to an analysis unit 10 illustrated schematically in FIG. 3. The analysis unit 10 may be implemented by a computer program executed in a computer apparatus or may be implemented by a dedicated hardware device, or any combination thereof. In either case, the data used by the method is stored in a memory in the analysis unit 10. The computer apparatus, where used, may be any type of computer system but is typically of conventional construction. The computer program may be written in any suitable programming language. The computer program may be stored on a computer-readable storage medium, which may be of any type, for example: a recording medium which is insertable into a drive of the computing system and which may store information magnetically, optically or opto-magnetically; a fixed recording medium of the computer system such as a hard drive; or a computer memory.

The analysis unit 10 and the measurement system are therefore connected and together constitute an apparatus for analysing a polynucleotide. The method may be performed in an apparatus including the analysis unit 10 and a measurement system arranged as disclosed in any of WO-2008/102210, WO-2009/07734, WO-2010/122293 and/or WO-2011/067559. The analysis unit 10 may also provide control signals to the control circuit 8, for example to select the voltage applied across the biological pore 1 in the measurement system 8.

The analysis unit 10 performs the following steps.

Optionally, there may be a pre-processing step (not shown) to pre-process the input signal 11, for example by filtering.

In step S3, the input signal 11 is processed to identify successive states in the electrical measurements. This may be done by detecting the transitions between the states.

Changes between states can generally be detected using either of two approaches.

The first approach is to look for a short-term increase in the derivative of the signal. This is generally done by applying a low-pass filter to the derivative of the signal to suppress high-frequency noise (which the differentiation tends to amplify). One can then set a threshold on the derivative of the signal to detect transition points. A common simplification of this technique is to use a sliding window analysis whereby one compares the means of two adjacent windows of data. Shifts in the underlying signal can then be derived when a threshold is exceeded by some mathematical function of the data in the two windows. In the simplest case, this could be the absolute difference in mean signal between the two windows, or some more complex function such as the t-statistic from a two sample t-test.

The second general approach is to model the data-generating process. One such frequently used generative model in this context is the Hidden Markov Model. Generative models require more assumptions to be made about the state transitions, but when such information is available they can give more robust results.

The state detection step S2 may be performed using the method shown in FIG. 4 that detects the transitions between the states as follows.

In step S2-1, the input signal 11 is differentiated to derive its derivative.

In step S2-2, the derivative from step S2-1 is subjected to low-pass filtering to suppress high-frequency noise (which the differentiation tends to amplify).

In step S2-3, the filtered derivative from step S2-2 is thresholded to detect transition points between the groups of measurements, and thereby identify the transitions between the states.

A possible simplification of the state detection step is to use a sliding window analysis whereby one compares the means of two adjacent windows of data. A threshold can then be either put directly on the difference in mean, or can be set based on the variance of the data points in the two windows (for example, by calculating Student's t-statistic). A particular advantage of these methods is that they can be applied without imposing many assumptions on the data.

In step S3, the measurements in respect of each state are processed to derive values of one or more features that represent characteristics in respect of that state. The values in respect of each state are output as an analysis signal 12.

In the simplest approach for step S3, a single value is derived, for example the mean value of the electrical measurements of that state.

Alternatively, plural values are obtained in respect of features that represent the same or different characteristics. This increases the information content. Examples of features that may be used include: an average (a mean or a median or other average) of the group of measurements; the period of the group of measurements; a variance of the group of measurements; the distribution of the group of measurements, asymmetry information; the confidence of the measurements; or any combination thereof.

Step S3 has the result of deriving an analysis signal 12 that represents the input signal 11 with an amount of information that is reduced, but in which the significant characteristics of the signal are maintained.

In general, other methods may alternatively be used in place of steps S2 and/or S3 to derive the analysis signal 12. In particular, it is not necessary to specifically identify the states. It is even possible to use the input signal 11 directly as the analysis signal 12.

The analysis signal 12 is derived from the nucleotides of the expanded polynucleotide. As a result, portions of the analysis signal 12 are the clock signals derived from the clock nucleotides of each expanded unit, and portions of the analysis signal 12 are nucleotide signals derived from the at least one signal nucleotide.

The analysis signal 12 is further processed in steps S4 and S5 to identify the clock signals and nucleotide signals within the analysis signal 12.

In step S4, the analysis signal 12 is analysed to identify the clock signals derived from at least one of the clock nucleotides in respect of each nucleotide in the target polynucleotide. As the clock nucleotides have a predetermined sequence common to each nucleotide in the target polynucleotide, the clock signals are all derived from that common sequence. Accordingly, subject to the inherent variations in the measurement system described above, the clock signals are the same, or at least similar. This enables the clock signals to be identified as they form a periodic repeating pattern in the analysis signal.

Step S4 may be performed by comparing the analysis signal 12 with stored clock signal data 14 representing the expected form of the clock signal. That expected form is dependent on the measurement system and may be derived from experiments involving translocation of a designed polynucleotide through the nanopore. An example for a particular measurement system is described below.

The clock signals may be signals derived from all the clock nucleotides. In many cases, this might provide the best discrimination. Alternatively, the clock signals may be signals derived from less than all the clock nucleotides. Where signals provided by given clock nucleotides (for example, in some embodiments, the further nucleotides) are more clearly discriminated from the other parts of the analysis signal 12 than the signal provided by the remaining clock nucleotides (for example, in some embodiments, the restriction site), then the identified clock signals may be those signals provided by given clock nucleotides.

Where the electrical measurements are dependent on a k-mer, the clock signals may include parts of the analysis signal 12 that are derived from signal nucleotides in addition to clock nucleotides, typically being signal nucleotides that are adjacent to clock nucleotides in the expanded polynucleotides. This may reduce the discrimination provided by those parts of the clocks signals, whilst still allowing identification of the clock signal as a whole. Alternatively, the clock signals may be restricted to parts of the analysis signal 12 that are dependent only on clock nucleotides.

Step S4 may involve windowing the analysis signal 12 and deriving a measure of similarity between the stored clock signal data 14 and windowed portions of the analysis signal 12. Detection of the clock signal occurs when the measure of similarity exceeds a threshold. Any conventional measure of similarity may be used for example a distance measure.

In step S5, the analysis signal 12 is analysed to identify the nucleotide signals derived from the at least one signal nucleotide in respect of each nucleotide in the target polynucleotide. Since the clock nucleotides and the at least one signal nucleotides are in a predetermined order, the nucleotide signals may be identified relative to the positions of the clock signals identified in step S4. Thus, the clock signals are effectively used to parse the analysis signal 12 to identify the nucleotide signals.

In step S6, the nucleotide signals in respect of each nucleotide in the target polynucleotide are analysed to analyse the target nucleotide. This may be performed by comparing the nucleotide signals with stored reference data 15.

A variety of types of analysis may be performed in step S6 based on the fact that the at least one signal nucleotide in each expanded unit and hence the nucleotide signals derived therefrom are characteristic of the nucleotides in the target polynucleotide. Ideally, the expanded polynucleotide is designed having regard to the measurement system so that the nucleotide signal derived from the at least one signal nucleotide in respect of a single nucleotide in the target polynucleotide is characteristic of that single nucleotide in the target polynucleotide.

In some types of analysis in step S6, the nucleotide signals are analysed to estimate the identity of individual nucleotides in the target polynucleotide. In this case, the stored reference data 15 represents the possible forms of the nucleotide signals expected in respect of each possible identity of the nucleotide in the target polynucleotide of which the nucleotide signal may be characteristic. Those expected forms are dependent on the measurement system and may be derived from experiments involving translocation of a designed polynucleotide through the nanopore. An example for a particular measurement system is described below.

In this case, in step S6 each nucleotide signal may be compared with each possible forms of the nucleotide signal, to derive a measure of similarity therebetween. The nucleotide in the target polynucleotide may then be identified as the nucleotide in respect of which the measure of similarity indicates the most similarity. Any conventional measure of similarity may be used for example a distance measure.

This technique reduces the number of possible signals to be discriminated even when the electrical measurements from which the analysis signal 12 is derived are dependent on a k-mer of the expanded polynucleotide. This is because the at least one signal nucleotide in each expanded unit is characteristic of the nucleotide in the target polynucleotide. Where electrical measurements are dependent on any clock nucleotide as well as a signal nucleotide, the common sequence of the clock nucleotides reduces the variation in possible sequences to be represented. Where plural signal nucleotides are used, since the have a sequence that is characteristic of the nucleotide in the target polynucleotide, then the number of possible nucleotide sequences is reduced compared to the total number of states possible to derive from a nucleotide sequence of the same length as the plural signal nucleotides. That is, step S6 may only need to discriminate between n nucleotide signals even though the electrical measurements are dependent on k nucleotides of the expanded polynucleotide. This may be viewed as reducing measurements of k-mers to measurements of single nucleotides.

Alternatively, the analysis step S6 may use a probabilistic method, for example an analytical technique as disclosed in detail in International Patent Application No. PCT/GB2012/052343 that refers to a model stored in the analysis unit 10 to estimate the identity of the at least one signal nucleotide, and hence the corresponding nucleotide in the target nucleotide, based on the likelihood predicted by the model of the nucleotide signal being produced. In this case, when using plural signal nucleotides, the probabilistic method is simplified in that the set of allowed states for the nucleotide signal is reduced.

In a non-limitative embodiment the method of estimating the sequence of the plural signal nucleotides may comprise providing a model comprising for a set of possible k-mers: transitions weightings representing the chances of transition from origin k-mers to destination k-mers and emission weightings in respect of each k-mer that represent the chances of observing given values of measurements for that k-mer and analysing the seris of measurements using an analytical technique that refers to the model and determining at least one estimated sequence of the plural signal nucleotides based on the likelihood predicted by the model of the series of measurements being produced by sequences of polymer units.

The model considers the possible k-mers. In the case of an unexpanded target polynucleotide sequence where each polymer unit may be one of 4 polymer units (or more generally n polymer units) there are $4^k$ possible k-mers (or more generally $n^k$ possible k-mers), unless any specific k-mer does not exist physically. For all k-mers that may exist, the emissions weightings take account of the chance of observing given values of measurements. The emission weightings represent probabilities of observing given values of each type of measurement for that k-mer. The transition weightings represent the chances of transitions from origin k-mers to destination k-mers, and therefore take account of the chance of the k-mer on which the measurements depend transitioning between different k-mers. The transition weightings may therefore take account of transitions that are more and less likely. By way of example, where k is a plural integer, for a given origin k-mer this may represent that a greater chance of a preferred transitions, being transitions to destination k-mers that have a sequence in which the first (k-1) polymer units are the final (k-1) polymer unit of the origin k-mer, than non-preferred transitions, being transitions to destination k-mers that have a sequence different from the origin k-mer and in which the first (k-1) polymer units are not the final (k-1) polymer units of the origin k-mer. For example, for 3-mers where the polymer units are naturally occurring DNA bases, state CGT has preferred transitions to GTC, GTG, GTT and GTA. By way of example without limitation, the model may be a Hidden Markov Model in which the transition weightings and emission weightings are probabilities.

This allows the series of measurements to be analysed using an analytical technique that refers to the model. At least one estimated sequence of polymer units in the polymer is estimated based on the likelihood predicted by the model of the series of measurements being produced by sequences of polymer units. For example but without limitation, the analytical technique may be a probabilistic technique.

However in the case of an expanded polynucleotide sequence, many or all of the nucleotides in the expanded polynucleotide are predetermined and therefore known in advance. This simplifies the model enormously and therefore the amount of computation required. This enables the use of nanopores that might be otherwise not be considered. For example, in the case of measurement of an unexpanded target polynucleotide using a nanopore whose measurement signal is dependent upon a k-mer where k is 10, the number of possible k-mers that would need to be considered by the model would be $4^{10}$. The transition matrix considered by the model would have $1.6 \times 10^{21}$ variables, namely the probability of transition from any one of $4^{10}$ k-mers to any one of $4^{10}$ k-mers, which would be computationally exceptionally demanding. In the case for example of the measurement of an expanded polynucleotide using a nanopore whose measurement signal is dependent upon a k-mer where k is 10, wherein each nucleotide of the target polynucleotide is expanded by an additional 10 nucleotides of which 9 are predetermined, such as disclosed in conversion sets A and B, the number of the possible k-mers that would need to be considered would be of the order of 36 and the transition matrix would be of the order of 103.

In other types of analysis in step S6, the nucleotide signals are analysed to determine the identity of the target polynucleotide. This may be achieved by reference to the overall sequence of nucleotide signals that corresponds to the overall sequence of the target polynucleotides, without necessarily estimating the identity of each nucleotide in the target polynucleotide.

In this case, the stored reference data 15 may represent one or more sequences of nucleotide signals in respect of one or more target polynucleotides.

Step S6 may involve a comparison of the sequence of nucleotide signals with the or each sequences of nucleotide signals represented by the stored reference data 15, to derive a measure of similarity therebetween. The measure of similarity may be used to identify the target polynucleotide.

The stored reference data 15 and the sequence of nucleotide signals may thus be considered as feature vectors, between which a comparison is made. The comparison is may employ the same techniques as the comparison of feature vectors in U.S. Patent Appl. No. 61/599,573 (N.116109/ONT IP 027) which is incorporated herein by reference.

The nucleotide signals may be analysed by deriving from the nucleotide signals, a feature vector of time-ordered features representing characteristics of the measurements and determining similarity between the derived feature vector and at least one other feature vector in order to determine the identity of at least a region of the target polynucleotide. The at least one other feature vector may be stored reference data. The plural parts of the derived feature vector may be compared to all, parts or plural parts of the stored reference data.

The stored reference data may be a pre-stored library or may be determined contemporaneously from other target polynucleotides under investigation. Step S6 may be implemented in a variety of manners to derive useful information about the target polynucleotides, including the corresponding examples disclosed in U.S. Patent Appl. No. 61/599,573 (N.116109/ONT IP 027).

There will now be discussed some of the mathematical techniques that may be applied in step S6 to determine similarity.

One approach is to modify existing pairwise dynamic programming sequence alignment algorithms e.g. the Needleman-Wunsch algorithm for global alignment or the Smith-Waterman algorithm for local alignment.

The modifications may include replacing the substitution matrix with a distance measure operating on the feature vector. For example the distance measure may be a measurement of the absolute difference in current between the data points. The distance function could also consider multiple measurements at each position e.g. mean and variance of a current measurement.

Modification may also be made to the to the gap scoring mechanism as are known in the art, for example constant gap penalties, linear gap penalties or affine gap penalties.

These algorithms output an alignment score that is a function of the two feature vectors, the distance function and the gap penalties. The alignment score can be used to determine similarity.

These modified alignment algorithms can be used for clustering, consensus building, and pattern matching although other methods can also be used to achieve these tasks.

Multiple alignment algorithms may also be modified in similar ways to those described for pairwise alignments.

Rather than match feature vectors by using gapped alignment techniques as described above, an alternative approach is to represent the feature vector in terms of shorter subvectors, typically comprising consecutive entries in the feature vector. For example, if the feature vector was (1,2, 3,4,5) then we could represent it by length 3 sub-vectors to give the new representation {(1,2,3), (2,3,4), (3,4,5)}. For our application the sub-vectors are frequently considerably longer (>10) so maintaining much of the time-ordering information.

Similarity of feature vectors on the basis of sub-vectors is then defined on the basis of how closely the set of sub-vectors match. This has the potential to be a more efficient means of comparison than gapped alignment type algorithms, since we may compare sub-vectors directly without allowing for gaps.

If the feature sub-vectors are suitably discretized (for example by rounding each number to the nearest 0.1) then exact or partial matches of sub-vectors may be used, and similarity calculated in terms of what proportion of sub-vectors match or partially match. Discretisation also enables integer arithmetic to be used for comparison. Alternatively hash functions may be applied to sub-vectors to give fixed length "fingerprints" (see for instance Karp, R., Rabin, M. (1987) "Efficient randomized pattern matching algorithms"/ IBM J. Res. Development 31:249-260.) denoting presence or absence of sub-vectors which can be rapidly compared.

Similar ideas in terms of matching sub-strings are used by algorithms like BLAST (Altschul, S. F., Gish, W., Miller, W., Myers, E. W. & Lipman, D. J. (1990) "Basic local alignment search tool." J. Mol. Biol. 215:403-410.) that split data into short fragments and match these against a large library.

An alternative approach is to use an HMM (Hidden Markov Model) Viterbi path as follows.

In general, alignment-based and sub-vector based measures of pairwise similarity treat the pair of feature vectors that are being compared in the same way. The result is that given a pair of feature vectors A and B, the similarity of A to B is equal to the similarity of B to A.

However, where one of the feature vectors to be compared is a library feature vector, it is natural to treat the problem as if that feature vector were the "model" or "training sequence". In this case, an alignment can be performed using HMM methods with models constructed in a similar manner to the "forced path" training models described previously (U.S. 61/538,721, GB 1117574.2). Algorithms other than Viterbi that are known in the art may also be applied, for example the Forwards-Backwards algorithm. As in the case of alignment algorithms, there is an output score that can be used as the measure of similarity. In the case of Viterbi this is the total likelihood of the path. The total likelihood is not guaranteed to be equal if we swapped the roles of the two feature vectors, however for classification problems in particular, this is not generally an issue.

EXAMPLES

There is now explained a specific example of the present method.

This example is designed for a measurement system in which the nanopore is MspA and Phi29 is used to control the translocation.

Conversions sets were designed to change one nucleotide of a target polynucleotide into an expanded unit. Conversion set A is an example of a conversion set. The following table illustrates the conversion of possible expanded units in respect of each target nucleotide (base).

Conversion Set A:

| Target Base | Expanded Unit | SEQ ID NO: |
|---|---|---|
| G | CTTTGGATGAG | 17 |
| T | CTTTGGATGTT | 18 |
| A | CTTTGGATGTA | 19 |
| C | CTTTGGATGTC | 20 |

Each expanded unit comprises clock nucleotides having a predetermined sequence CTTTGGATG that is common to each target nucleotide. That predetermined sequence comprises a restriction site GGATG of a restriction enzyme (in this example, for the enzymes BseGI and BtsCI).

That predetermined sequence also comprises further nucleotides CTTT that extend the predetermined sequence, thereby extending the resultant clock signal and making it easier to detect in the analysis signal 12. The restriction site provided by the enzyme is a repeating code. This could provide a clock signal in itself but the clock signal can be improved by the further nucleotides. The specific sequence CTTT in this example gives rise to a recognisable and measurable clock signal. The sequence CTTT of the further nucleotides was chosen as previous experiments had shown that CTTT gives a large negative deflection for the baseline MspA pore to be used in the measurement system, and therefore provides a clock signal that was easily recognisable. The choice of clock signal nucleotides would most likely depend upon the measurement system, including the nanopore. In the example given, the clock sequence CTTT is 4 nucleotide bases, however in principle it could be any number of one or more.

Each expanded unit further comprises two signal nucleotides that have sequence that is characteristic of the target nucleotide. In particular, the signal nucleotides are AG, TT, TA, or TC being characteristic of target nucleotides G, T, A, or C, respectively.

The signal nucleotides were chosen to try to separate out current levels of the four expanded units.

Synthetic strands, being expanded nucleotides, were obtained that encoded three repeats of each expanded unit. For example of a strand for the examining C is:

(SEQ ID NO: 21)
5'-CTTTGGATGTCCTTTGGATGTCCTTTGGATGTC-3'

The strand has a 5' single stranded overhang in order to thread into the nanopore, referred to as a "leader section". This is typically 30-50 nucleotides in length and preferably low in secondary structure. An example of a leader section is:

(SEQ ID NO: 22)
5'-CCCCCCCCCCCCACCCCCCCCCCCCACCCCCCCCCCCC-3'

The last element of the strand design is the end section. As the reader element of the nanopore can be some distance from the enzyme, some nucleotides are required at the end of the strand to ensure that all of the expanded units pass through the reader element. For the experiments that use Phi29 to control the strand motion and MspA as the base reader, the distance between the reader element and the enzyme unzipping site is 12-14 nucleotides. The end section must also be sufficiently long that the enzyme and DNA do not dissociate before the expanded units have passed through the pore. An example of an end section is:

```
                                          (SEQ ID NO: 23)
5'-CATTCAGATCTCACTATCGCATTCTCATGCAGGTCGTAGC-3'
```

The resultant strand for a CCC expansion is:

```
                                           (SEQ ID NO: 7)
5'-CCCCCCCCCCCACCCCCCCCCCCACCCCCCCCCCCCTTTGGATG

TCCTTTGGATGTCCTTTGGATGTCCATTCAGATCTCACTATCGCATTCTC

ATGCAGGTCGTAGC-3'
```

For expansions of longer target polynucleotides, the end section and the leader could remain the same, but the middle section would contain more expanded units.

Following experiments on the initial conversion set (see below), conversion set B was designed to give better separation of the four standard nucleotides, as shown in the following table.

Conversion Set B:

| Target Base | Expanded Unit | SEQ ID NO: |
|---|---|---|
| G | CTTTGGATGAG | 17 |
| T | CTTTGGATGCT | 24 |
| A | CTTTGGATGTA | 19 |
| C | CTTTGGATGTC | 20 |

Conversion set B is the same as conversion set A except that the set of signal nucleotides are changed to be AG, CT, TA, or TC, being characteristic of target nucleotides G, T, A, or C, respectively. As explained below, conversion set B produced excellent separation of the four nucleotides for the MspA pore, allowing each of the four expanded units to be resolved Sample preparation was performed in accordance with the specific example described below.

Electrical measurements were obtained using a measurement system 8 as shown in FIG. 1. In the basic setup, a lipid membrane was formed to separate two aqueous chambers, containing an electrolyte such as KCl. Electrodes were placed in each aqueous reservoir, a potential was applied across the membrane and the ionic current between the two chambers was monitored. A single channel was inserted into the membrane which was observed as a step change in the current flow.

Once a single channel was obtained, a 10× concentration stock solution containing the DNA analyte and the Phi29 DNAP was added to the solution. Enzyme-DNA binding events were observed and multiple current states were seen as the DNA unzipped through the pore. Runs were obtained at constant applied potential, occasionally reversing the potential to unblock the pore. Multiple DNA molecules were moved through the nanopore over the duration of the run.

Typical run conditions were: MS-(B1)$_8$, 400 mM KCl, 10 mM Hepes, pH 8.0, 1 mM EDTA, 1 mM DTT, +180 mV. The final concentration of DNA analyte was run at 100 nM with 200 nM of Phi29 DNAP. Experiments were terminated after sufficient data was acquired; typically runs of 30 mins to 1 hour were sufficient.

Current levels were extracted from the raw data to generate an event trace. The levels from multiple molecules were aligned together to form a consensus plot of that molecule.

Once the changes in current level have been detected, and the data is thus reduced to a sequence of discrete states, alignment of the states found for each DNA capture sequence can be performed to produce a single consensus sequence for the strand. A number of alignment methods exist that can be used for this purpose, including the Needleman-Wunsch and the Smith-Waterman algorithms, both based on the principles of Dynamic Programming. In cases where the number of possible states is small and each state is constrained to allow only a small subset of permitted subsequent states, more highly optimized heuristic or probabilistic methods can used.

The electrical measurements were analysed as follows.

Current levels from the consensus plots were assigned to the clock signal or the nucleotide signal.

Conversion set A was analysed first.

Individual nanopore experiments were conducted for each of the four control strands in conversion set A. The strands were run through the MspA pore under standard unzipping conditions: MS-(B1)$_8$, 400 mM KCl, 10 mM Hepes, pH 8.0, 1 mM EDTA, 1 mM DTT, +180 mV, 100 nM DNA, 200 nM Phi29 DNAP.

The DNA was designed as described above and in FIG. 5 which is a diagram of an example DNA strand used in experiments where the DNA as unzipped through a nanopore. The first region 41 is the leader section, the next region 42 is the expanded unit region (in this case, 3 bases have been converted), the final region 43 is the end section. The lower region 44 is complementary DNA. The Phi29 enzyme binds to the single strand/double strand junction.

Figure 6:
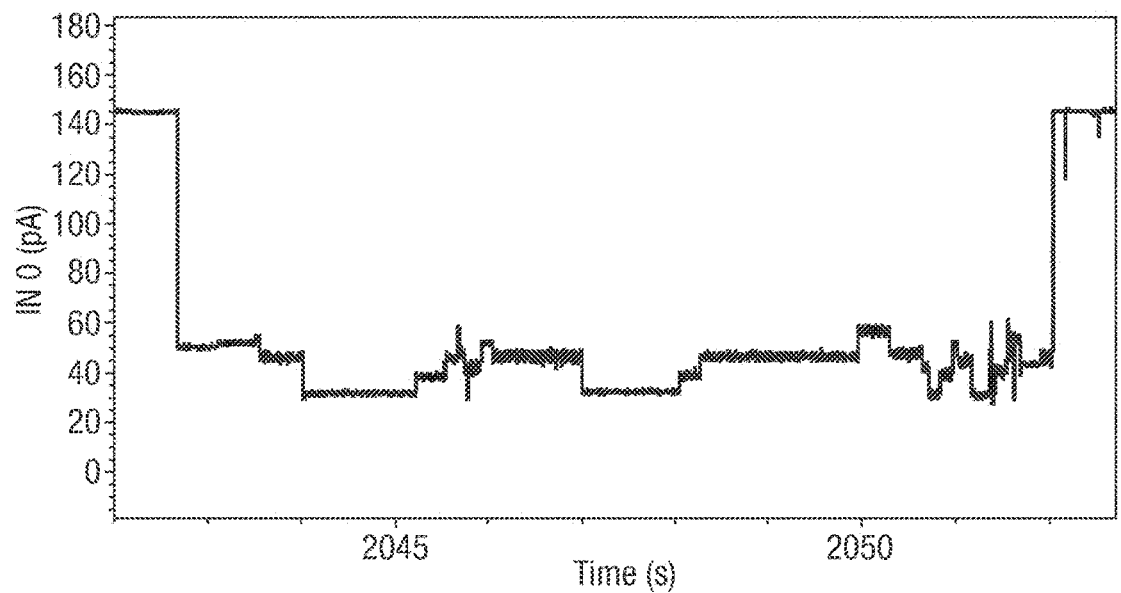
FIG. 6 is an example of a current trace for ion current measurements on the DNA strand of FIG. 5.

Single molecules events could be identified when the current dropped below the open pore current and multiple current levels were observed. When the strand is unzipped completely, the enzyme-DNA complex dissociates and the current returns to the open pore level as shown in FIG. 6 which is an example of a current trace for unzipping the DNA in FIG. 5 through the nanopore using Phi29. The trace is acquired at 20 kHz and software filtered down to 1 kHz for display purposes.

Figure 7:
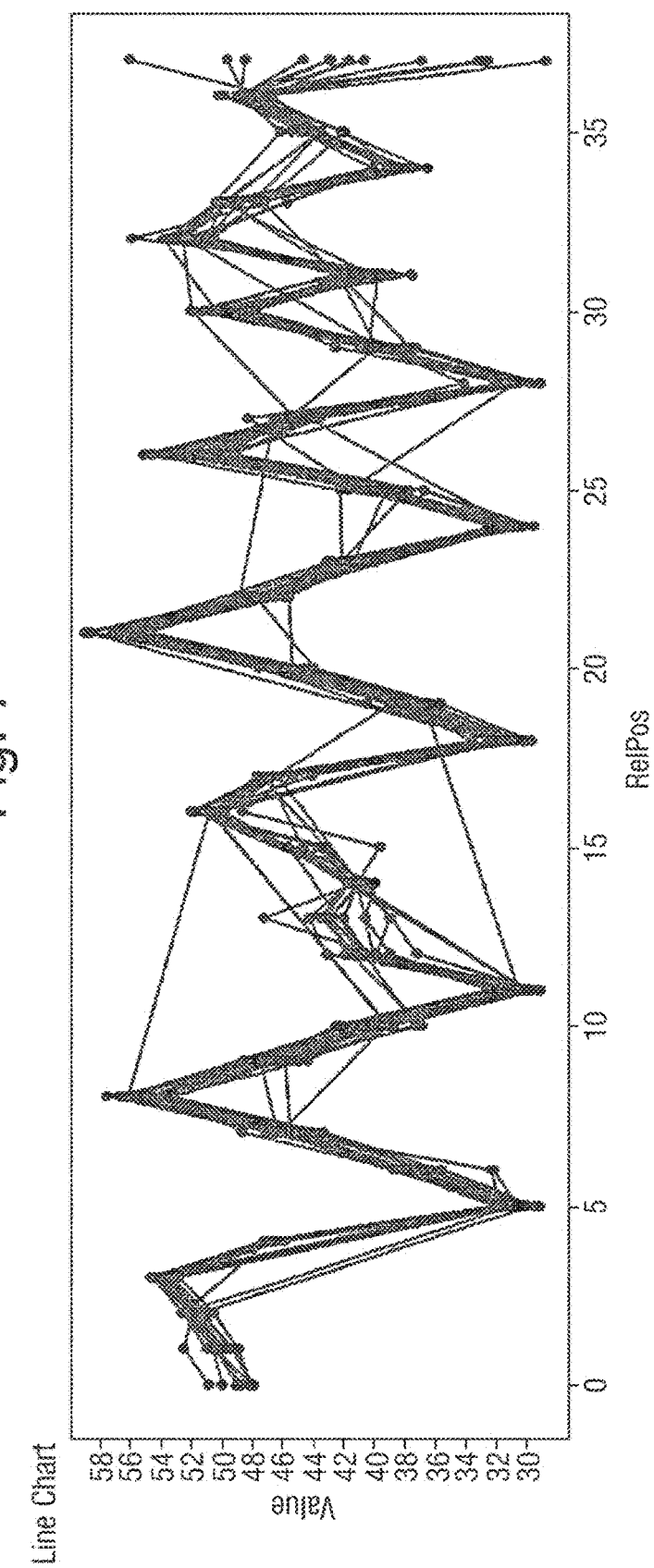
FIG. 7 is a consensus plot of current measurements generated from single molecules of DNA from FIG. 5.

The state levels from these strands can be extracted using the techniques described above. These levels can then be aligned to a consensus to generate plot from multiple single molecule reads as shown in FIG. 7 which is a consensus plot generated from single molecules of DNA from FIG. 5. In FIG. 7, the x-axis is for the relative position (or event index), the y-axis is the observed current in pA.

The consensus plot of FIG. 7 clearly shows a number of distinct features.

Firstly, the clock signal derived from the clock nucleotides can clearly be discriminated. The first peak at a relative position of 3 is indicative of the single A in the polyC leader moving through the reader element of the pore. The drop to 30 pA at position 5 represents the CTTT motif of the clock nucleotides moving through the reader element and is indicative of the lowest current given by the "clock". The return to around 56 pA occurs when the restriction site of the clock nucleotides is read.

Secondly, the different nucleotide signals can be seen to characterise the possible target nucleotides. The last section of the trace is a combination of the latter part of the restriction site and the unique encoding section, in this case TA. The lowest current level at position 11 occurs from the TGT triplet in the read head, with the TG coming from the restriction site and the final T resulting from the unique TA encoding. The consensus plot therefore shows three "clock" signals at positions 5, 18 and 28. The first of the two unique sections can be seen between the clocks, the unique region from the third base encoding is followed by nucleotides in the end section which will interfere with the current levels.

In FIG. 7, the clock signal was determined to appear at positions 5, 18 and 28. In an ideal system the clocks would be regularly spaced. However, it is notable that even the imperfect measurements of FIG. 7 produce a clock signal that can be discriminated.

Figure 8:
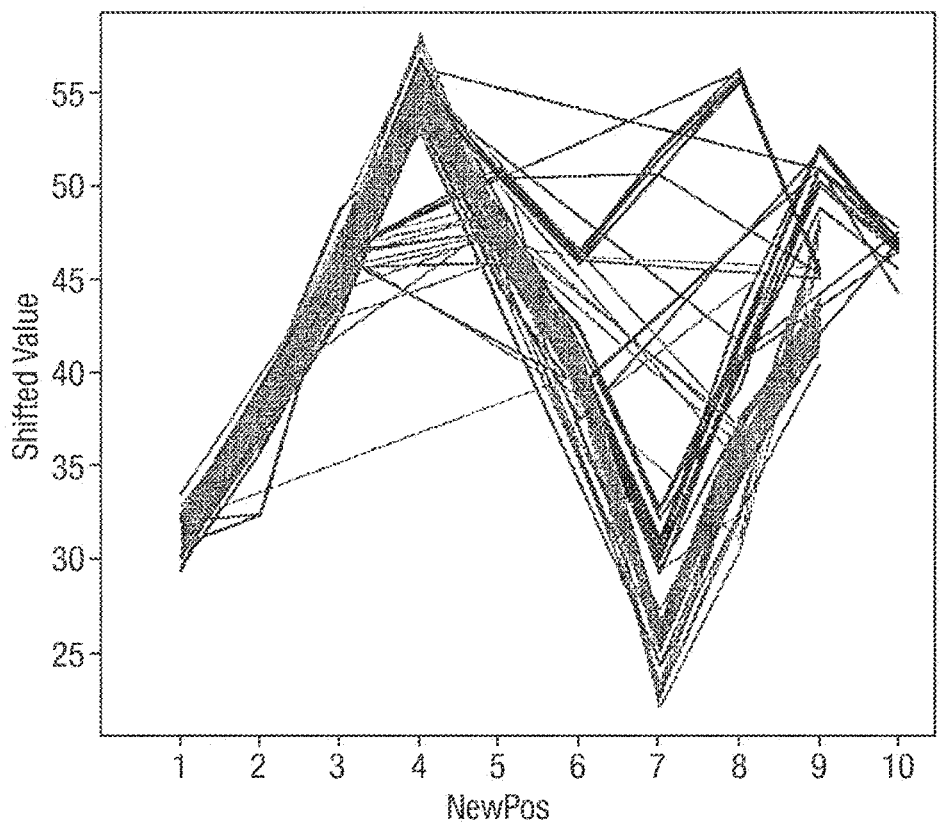
FIG. 8 is a consensus plot of current measurements of each expanded unit in a conversion set A.

Control strands from all four standard DNA bases were acquired (SEQ ID NOs: 1 to 8). The consensus plots were generated and the current levels from a single expanded unit were plotted. The results for G. T. A. and C are shown in FIG. 8 which is a consensus plot of current levels of each expanded unit in conversion set A.

Figure 9:
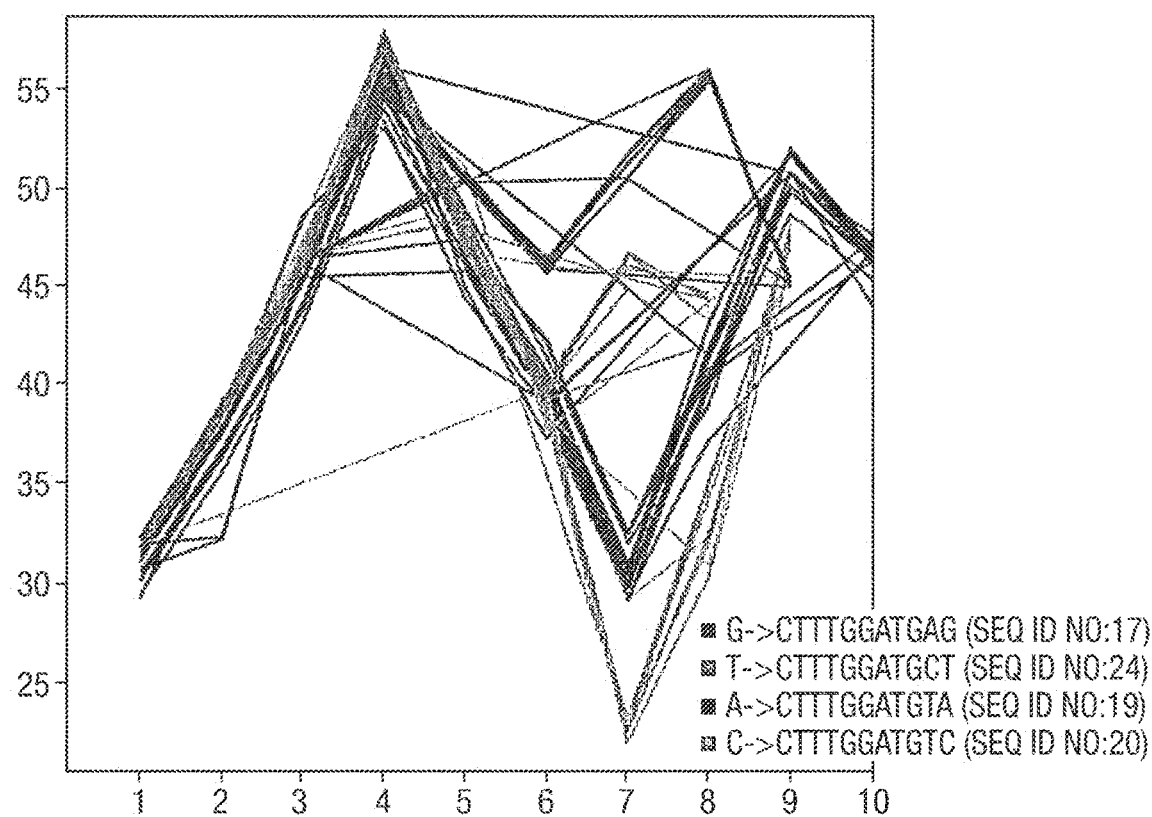
FIG. 9 is a consensus plot of current measurements of each expanded unit in a conversion set B (SEQ ID NOs: 17, 24, 19 and 20)

It is clear from FIG. 9 that for conversion set A that there is good distinction between the converted G and T, however the converted A and the converted T overlap with each other and need to be resolved. Therefore, although the initial conversion set A did show the clock signal, the resolution between the unique sections was not ideal. This was improved by the modified design of expanded units in conversion set B as follows.

To further separate the four converted bases used in conversion set A, the encoding for T was changed from CTTTGGATGTT (SEQ ID NO: 18) (conversion set A) to CTTTGGATGCT (SEQ ID NO: 24) (conversion set B). All the other three bases remained the same between the two conversion sets. A strand was design to encode TTT (SEQ ID NO: 9 and SEQ ID NO: 10) and was tested as described for conversion set A above.

The current levels for each encoded signal were extracted and plotted together as shown in FIG. 9 which is a consensus plot current levels of each expanded unit in set B.

Figure 10:
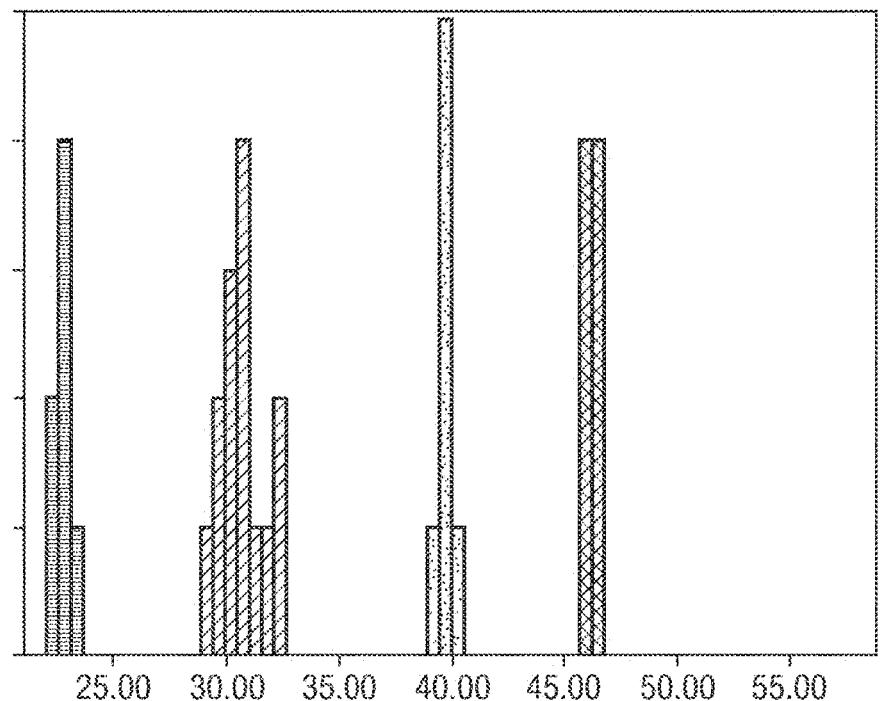
FIG. 10 is a histogram of current levels for the minimum current level following the clock for each expanded unit in conversion set B.

It is clear from this data that each of the four encodings gave distinct current signals. In particular, the minimum deflection after the "clock" signal gave current levels that were very well separated as shown in FIG. 10 which is a histogram of current levels for the minimum current level following the clock for each expanded unit in set B. The levels for C. A. T and G are in separated clusters from left to right across FIG. 10.

This demonstrates that conversion set B can be used as a conversion set to distinguish the four main nucleotides found in DNA.

To test the concept of nanopore DNA sequencing with this approach, a number of synthetic DNA strands were ordered which contained 10 expanded units (SEQ ID NO: 11 to SEQ ID NO: 16). Due to the repeating sequence of the common elements in the conversions sets, hybridisation of the two synthetic strands may be problematic. Each set of strands were hybridised by heating in an aqueous solution to 95° C., followed by a slow overnight cool to room temperature in a PCR machine. However, analysis was performed on an Agilent 2100 Bioanalyser which did not show the desired single hybridisation product. These hybridisation issues would not be a problem for DNA prepared by the methods described in the sample preparation section as the complementary DNA would be formed by enzyme synthesis. If required, there are many hybridisation schemes that could be employed to improve the quality of hybridisation of these strands.

Figure 11:
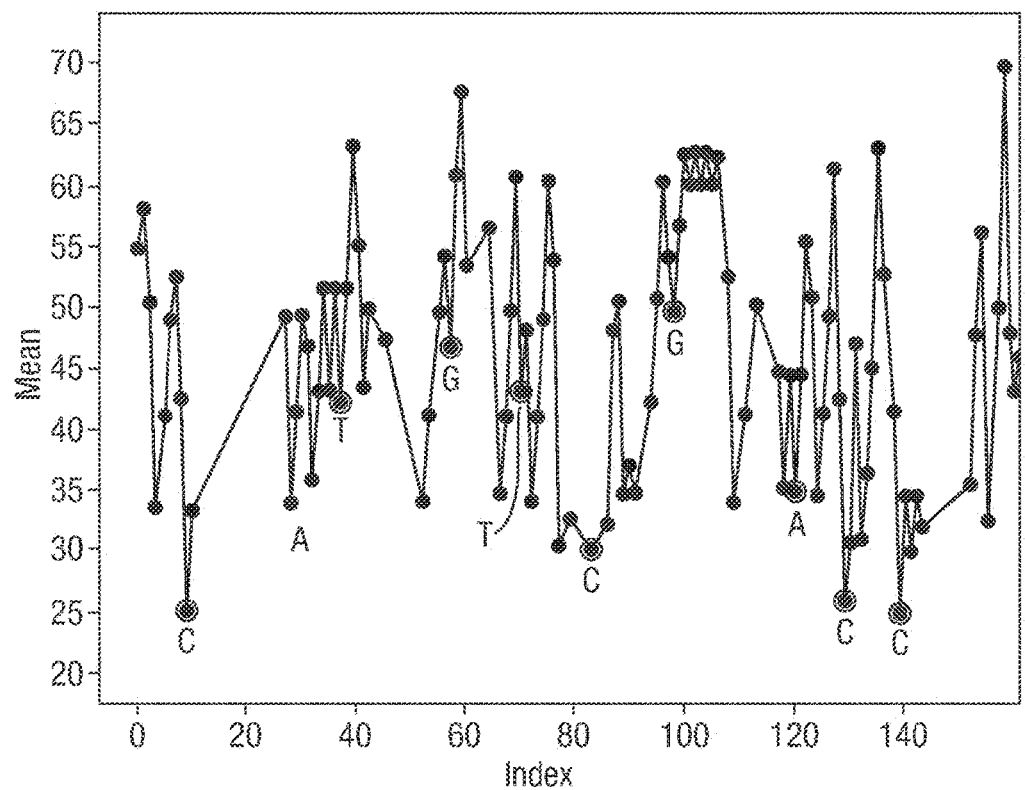
FIG. 11 is a plot of events from a single strand of DNA.

Nanopore unzipping runs were performed on these strands as described above. The current levels were converted into event states as described above. For a single strand, the distinct elements of the expanded units could be identified as shown in FIG. 11 which is a plot of states from a single strand of DNA being unzipped through the nanopore (conversion set B. SEQ ID NO: 15 and SEQ ID NO: 16, converted sequence is CATGTCGACC (SEQ ID NO: 25)). Clock signals are discriminated from the other states. The current levels following the clock signal can be used to identify each of the four converted nucleotides. Not all states are seen due to some issues with movement through the pore and possible hybridisation issues.

The data from the single molecule event trace shows that the states can be resolved sequentially for each of the four bases and that the current levels can be assigned to these bases with a high confidence. Movement or hybridisation issues prevent all of the states from being observed, both of these issues that can be improved in development.

Figure 12:
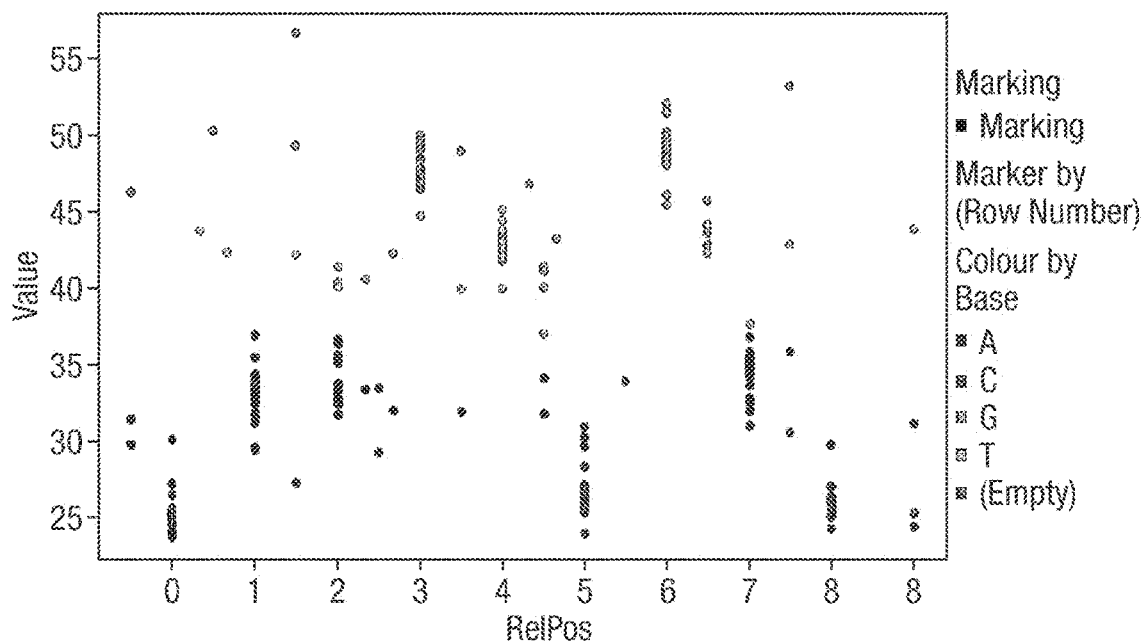
FIG. 12 is a plot of unique section current measurements (indicative of each of the four original DNA bases) taken from a consensus of single molecules from a strand containing ten expanded units.

Multiple single molecule events can grouped together into a consensus plot as described above. The consensus plot can then be used to call the bases based on the control set described above, as shown in FIG. 12 which is a plot of unique section current levels (indicative of each of the four original DNA bases) taken from a consensus of single molecules from a strand containing ten expanded units (set B, CATGTCGACC (SEQ ID NO: 25), SEQ ID NO: 15 and SEQ ID NO: 16). The information described above in FIG. 12 shows predicts the sequence CAAGTCGAC for the original strand based as read from the expanded units of the DNA moved through the nanopore (SEQ ID NO: 15 and SEQ ID NO: 16). The unconverted sequence of the strand was CATGTCGACC (SEQ ID NO: 25). Therefore the actual and the measured sequence correlate strongly. There are two main differences; the base call for the third base is clearly wrong (measured A, actual T), and the last base is missed. The miscall has been investigated and is due to an error in alignment, while the last base is known to be a problem due to the design of the end section.

This data indicates that sequences of DNA can be extracted using a nanopore by employing sample preparation methods to encode a sequence into a polymer that can easily be read by the nanopore.

A specific example of a method of preparing the expanded polynucleotide will now be described.

The expanded polynucleotide is prepared from the target polynucleotide using a restriction enzyme, in this case a Type IIS restriction enzyme.

The expansion process is achieved by performing cycles of a multi-step process, in which each cycle removes a single nucleotide from the 5' terminus of template molecules and attaches an expanded unit onto the 3' terminus. One cycle of the multi-step process is shown schematically in FIG. 13. The process is most simply explained by considering a single stranded target polynucleotide 20.

Figure 13:
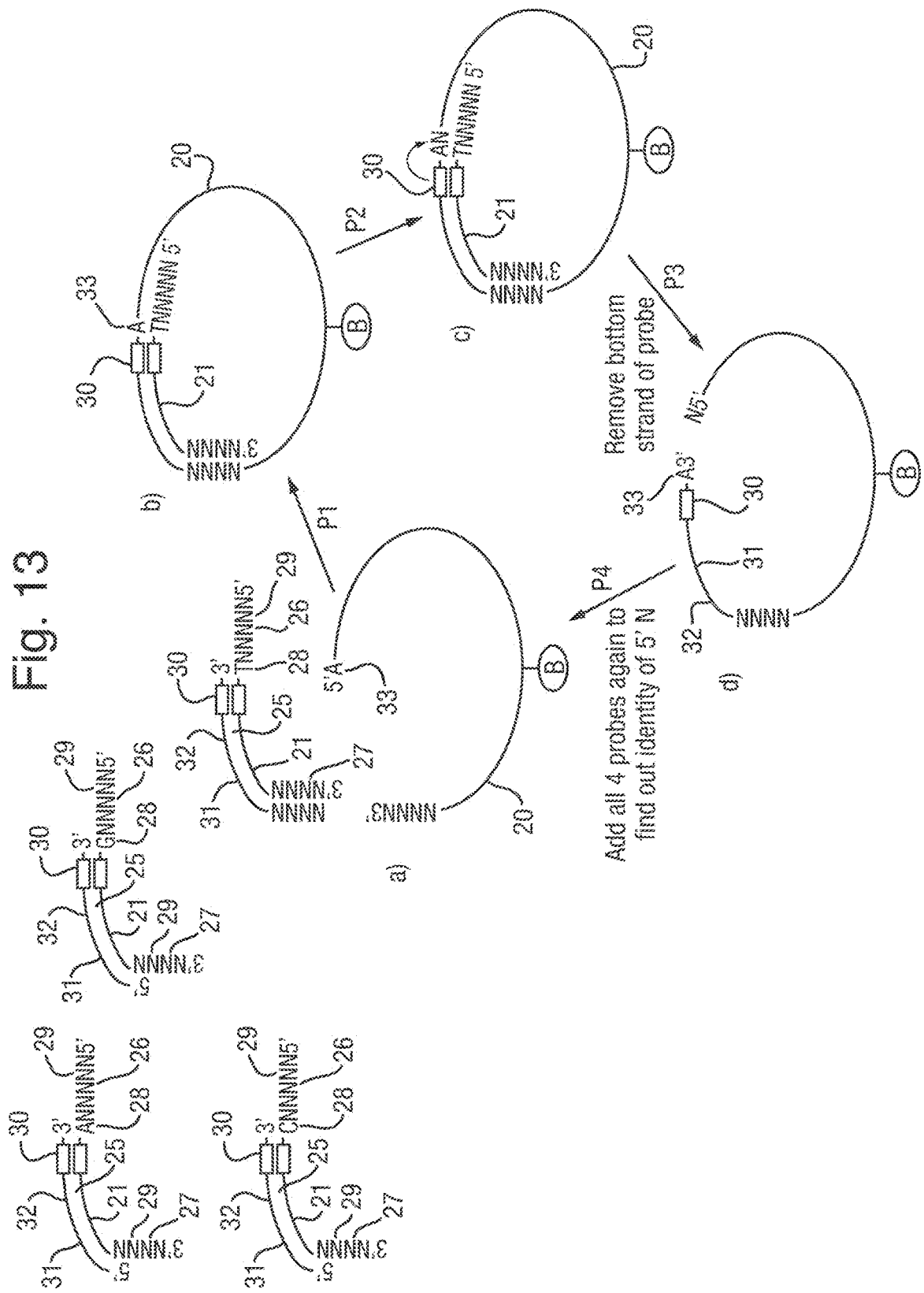
FIG. 13 is a schematic diagram of polynucleotide strands processed during a sample preparation technique.

Template DNA in a sample is fragmented, e.g. by sonication, to approximately 500 nucleotides to provide the target polynucleotide 20. FIG. 13(*a*) shows the example for illustrative purposes that the nucleotide 33 at the 5' end of the target polynucleotide 20 has identity A.

A library of hybridised adapters 21 are prepared in respect of each possible identity of a nucleotide in the target polynucleotide 20. Each adapter 21 consists of an invariant double stranded section 25, but one strand additionally possesses degenerate overhangs 26 and 27 at the at 5' and 3' ends, respectively.

The strand 32 of the double stranded section 25 without the degenerate overhangs 26 and 27 can become a clock sequence in the expanded polynucleotides, and thus comprises: a restriction site 30 for the restriction enzyme, being GGATG in the above example that the restriction enzyme is BseGI; and at least one further nucleotide 31, being CTTT in the above example.

The overhang 26 at the 5' end starts with a complementary polynucleotide 28 that may be any possible nucleotide, examples being shown in FIG. 13 where the complementary polynucleotide 28 have identities T. G. A and C.

The overhangs 26 and 27 at the at 5' and 3' ends additionally comprise degenerate nucleotides 29 (generically named as Ns) which, if complementary to respective the nucleotides of the target polynucleotide 20, will hybridise to form a circular structure. Given that the respective ends of the target polynucleotide 20 are unknown, a large number of adapters 21 to 24 need to be provided such that one of them will bind. Thus, the set of adapters 21 to 24 form a complex library, in which all possible combinations of nucleotide are represented at the degenerate positions, to allow annealing and ligation to templates of any sequence of the target polynucleotide 20.

In this example, the overhang 26 at the 5' end is shown with five degenerate nucleotides 29 and the overhang 27 at 3' end is shown with four degenerate nucleotides 29, but this is not essential and in general the numbers of degenerate nucleotides 29 may be chosen to provide reliable annealing and having regard to digestion by the restriction enzyme. Typically, the number of degenerate nucleotides 29 may be from four to six.

In principle, the number of adapters 21 in the library could be reduced by replacing one or more the nucleotides of the overhangs 26 and 27 by a nucleotide that could universally recognise any base combination. Inosine is capable of pairing with any of the four bases A. G. C. T and may be a good choice.

In step P1, the library of hybridised adapters 21 are mixed with the target polynucleotide 20. This causes one of the hybridised adapters 21 in the library to circularise target polynucleotide 20 by means of the overhangs 26 and 27 having the appropriate sequences annealing to both ends of the target polynucleotide 20. This is shown in FIG. 13(*b*) for the example that the target polynucleotide 20 has nucleotide with identity A at its 5' end and so circularisation occurs with an adapter 21 having a complementary polynucleotide 28 with a complementary identity T.

In step P2, the circularised target polynucleotides 20 are digested with the restriction enzyme, such as BseGI. Due to the location of the restriction site 30, the restriction enzyme cleaves the target polynucleotide 20 immediately to 3' side of the nucleotide at the 5' end of the target polynucleotide 20, thereby cleaving off the nucleotide 33, as shown in FIG. 13(*c*).

In step P3, the target polynucleotide 20 is denatured to remove the strand of the adapter 21 having the degenerate overhangs 26 and 27, as shown in FIG. 13(*d*). This regenerates the target polynucleotide 20 as a linear template. The regenerated target polynucleotide 20 has at is 3' end an expanded unit comprising the clock sequence from the adapter 21 comprising the restriction site 30 and the at least one further nucleotide 31; and the nucleotide 33 previously at the 5' end of the target polynucleotide 20. The restriction enzyme only works in the presence of a hybridised polynucleotide such that once the strand of the adapter 21 having the degenerate overhangs 26 and 27 is removed, the restriction enzyme does not act on the expanded target polynucleotide 20 in its single stranded form.

In this manner, in one cycle, the nucleotide 33 at the 5' end of the target polynucleotide 20 is expanded and transferred to the 3' end. The cycle is performed repeatedly to expand a sufficient number of the nucleotides. In order to perform another cycle, in step P4, the reaction product is separated from the other components by washing to step P1 is performed again.

The typical number of cycles that this would be repeated for would be around 30. The DNA fragments forming the target polynucleotide 20 themselves would typically be of length 400-500 nucleotides to allow them to be processed through the nanopore. Thus only a small number of nucleotides need be converted. Whilst the expanding process can be carried out consecutively (for example in a robotic fashion by attaching the product on beads to allow for easy separation), a vast number of target polynucleotides 20 can be processed concurrently in the same process.

The invention claimed is:

1. A method of analyzing a target polynucleotide that comprises at each nucleotide position a member of a set of different nucleotides, the method comprising:
   A) obtaining an expanded single-stranded polynucleotide that comprises a sequence of expanded units, wherein each expanded unit:
   a) ordinally corresponds to a particular nucleotide position of the target polynucleotide, and
   b) comprises:
      i) a clock nucleotide sequence, the clock nucleotide sequence being common among expanded units of the expanded polynucleotide, and ii) at least one signal nucleotide, the at least one signal nucleotide being indicative of the member of the set of different nucleotides at the particular nucleotide position;
   B) hybridising two or more single-stranded polynucleotides to the expanded single-stranded polynucleotide to form an expanded polynucleotide comprising two or more sections of double-stranded polynucleotide separated by single-stranded polynucleotide;
   C) translocating the expanded polynucleotide through a nanopore until a first section of double-stranded polynucleotide reaches the nanopore and halts translocation of the expanded polynucleotide;
   D) making electrical measurements dependent on the expanded polynucleotide within the pore;
   E) un-hybridising the first section of double-stranded polynucleotide such that translocation of the expanded polynucleotide through the nanopore continues; and
   F) determining the sequence of one or more regions of the target polynucleotide based on the measurements obtained in step D).

2. A method according to claim 1, wherein steps C to E are repeated with respect to a second and subsequent sections of double-stranded polynucleotide.

3. A method according to claim 1, wherein step B comprises hybridising a single-stranded polynucleotide to each expanded unit present in the single-stranded polynucleotide.

4. A method according to claim 1, wherein determining the sequence of the one or more regions of the target polynucleotide comprises deriving an analysis signal from the measurements obtained in step D.

5. A method according to claim 4, wherein determining the sequence of the one or more regions of the target polynucleotide further comprises analyzing the analysis signal by:
   identifying, within the analysis signal, clock signals, wherein each clock signal is derived from at least one of the clock nucleotides in the clock nucleotide sequence in an expanded unit ordinally corresponding to the clock signal; and
   identifying nucleotide signals, wherein each nucleotide signal is derived from the at least one signal nucleotide in an expanded unit ordinally corresponding to the nucleotide signal; and
   analyzing the nucleotide signals to analyze the target polynucleotide.

6. A method according to claim 5, wherein the nucleotide signal derived from the at least one signal nucleotide is indicative of the member of the set of different nucleotides at the particular nucleotide position of the target polynucleotide.

7. A method according to claim 5, wherein the step of analyzing the nucleotide signals comprises analyzing the nucleotide signals to determine the sequence of the target polynucleotide or one or more regions thereof.

8. A method according to claim 7, wherein the step of analyzing the nucleotide signals to determine the sequence of the target polynucleotide or one or more regions thereof comprises deriving, from the nucleotide signals, a feature vector of time-ordered features representing characteristics of the measurements and determining similarity between the derived feature vector and at least one other feature vector.

9. A method according to claim 5, wherein the step of analyzing the nucleotide signals comprises analyzing the nucleotide signals to determine the identity of individual nucleotides in the target polynucleotide.

10. A method according to claim 4, wherein the step of deriving an analysis signal comprises detecting states in electrical measurements, and deriving, from each state, at least one value representing a characteristic of the state to form said analysis signal.

11. A method according to claim 1, wherein the value of each measurement is dependent upon a k-mer, being a group of k nucleotide units where k is greater than one.

12. A method according to claim 11, where k is 7 or greater.

13. A method according to claim 1, wherein the clock nucleotide sequence comprises a restriction site for a restriction enzyme and at least one further nucleotide that extends the clock nucleotide sequence.

14. A method according to claim 1, wherein the at least one signal nucleotide consists of a single signal nucleotide.

15. A method according to claim 14, wherein the single signal nucleotide has the same identity as the member of the set of different nucleotides at the particular nucleotide position.

16. A method according to claim 1, wherein the at least one signal nucleotide consists of a signal nucleotide sequence of plural signal nucleotides, wherein the signal nucleotide sequence is indicative of the member of the set of different nucleotides at the particular nucleotide position.

17. A method according to claim 16, wherein one of the plural signal nucleotides has the same identity as the member of the set of different nucleotides at the particular nucleotide position.

18. A method according to claim 16, wherein the clock nucleotide sequence and the signal nucleotide sequence are in a predetermined order in which the signal nucleotide sequence is contiguous.

19. A method according to claim 1, wherein the electrical measurements comprise measurements of ion flow through the nanopore.

20. A method according to claim 1, wherein the nanopore is a biological pore.

21. A method according to claim 1, wherein said translocation of the polynucleotide through the nanopore is performed in a ratcheted manner in which successive nucleotides are registered with the nanopore.

22. A method according to claim 1, further comprising, before said step of making electrical measurements, expanding the target polynucleotide to form the expanded single-stranded polynucleotide.

23. A method according to claim 1, wherein at least one signal nucleotide of the at least one signal nucleotides has the same identity as the member of the set of different nucleotides at the particular nucleotide position.

24. A method according to claim 1, wherein at least one signal nucleotide of the at least one signal nucleotides is the complement of the member of the set of different nucleotides at the particular nucleotide position.

* * * * *